US010580530B2

(12) United States Patent
Rim et al.

(10) Patent No.: US 10,580,530 B2
(45) Date of Patent: Mar. 3, 2020

(54) DIAGNOSIS ASSISTANCE SYSTEM AND CONTROL METHOD THEREOF

(71) Applicant: MEDI WHALE INC., Seoul (KR)

(72) Inventors: Hyung Taek Rim, Seoul (KR); Seong Jung Kim, Seoul (KR); Tae Geun Choi, Seoul (KR)

(73) Assignee: MEDI WHALE INC., Seoul (KR)

( * ) Notice: Subject to any disclaimer, the term of this patent is extended or adjusted under 35 U.S.C. 154(b) by 0 days.

(21) Appl. No.: 16/359,902

(22) Filed: Mar. 20, 2019

(65) Prior Publication Data

US 2019/0221313 A1  Jul. 18, 2019

Related U.S. Application Data

(63) Continuation of application No. PCT/KR2018/009809, filed on Aug. 24, 2018.

(30) Foreign Application Priority Data

Aug. 25, 2017 (KR) ........................ 10-2017-0108232

(51) Int. Cl.
*G16H 50/20* (2018.01)
*G06T 7/00* (2017.01)
(Continued)

(52) U.S. Cl.
CPC ........... *G16H 50/20* (2018.01); *A61B 3/1176* (2013.01); *A61B 3/12* (2013.01); *A61B 5/7267* (2013.01);
(Continued)

(58) Field of Classification Search
None
See application file for complete search history.

(56) References Cited

U.S. PATENT DOCUMENTS

| 5,857,030 A * | 1/1999 | Gaborski ................. G06K 9/62 |
| | | 378/37 |
| 2006/0257031 A1* | 11/2006 | Abramoff ............ G06K 9/6277 |
| | | 382/224 |

(Continued)

FOREIGN PATENT DOCUMENTS

| JP | 2009-066015 A | 4/2009 |
| JP | 2011-212094 A | 10/2011 |

(Continued)

OTHER PUBLICATIONS

Maji, Debapriya, et al. "Ensemble of deep convolutional neural networks for learning to detect retinal vessels in fundus images." arXiv preprint arXiv:1603.04833 (2016). (Year: 2016).*

(Continued)

*Primary Examiner* — Andrae S Allison
(74) *Attorney, Agent, or Firm* — Fenwick & West LLP

(57) ABSTRACT

The present invention relates to a diagnosis assistance system for assisting diagnosis for a plurality of diseases based on a fundus image, the diagnosis assistance system including: a fundus image obtaining unit configured to obtain a fundus image; a first processing unit configured to, for the fundus image, obtain a first result related to a first finding of a patient using a first neural network model, a second processing unit configured to, for the fundus image, obtain a second result related to a second finding of the patient using a second neural network model, a third processing unit configured to determine, on the basis of the first result and the second result, diagnostic information on the patient, and a diagnostic information output unit configured to provide the determined diagnostic information to a user.

20 Claims, 30 Drawing Sheets

(51) Int. Cl.
*G06K 9/62* (2006.01)
*A61B 5/00* (2006.01)
*A61B 3/117* (2006.01)
*A61B 3/12* (2006.01)

(52) U.S. Cl.
CPC ......... *G06K 9/6256* (2013.01); *G06K 9/6262* (2013.01); *G06K 9/6268* (2013.01); *G06T 7/0014* (2013.01); *G06T 2207/20081* (2013.01); *G06T 2207/20084* (2013.01); *G06T 2207/30041* (2013.01); *G06T 2207/30101* (2013.01)

(56) References Cited

U.S. PATENT DOCUMENTS

| | | | | |
|---|---|---|---|---|
| 2011/0176710 | A1* | 7/2011 | Mattiuzzi | G06F 19/321 |
| | | | | 382/128 |
| 2012/0070049 | A1* | 3/2012 | Iwase | G06T 7/0012 |
| | | | | 382/128 |
| 2018/0214087 | A1* | 8/2018 | Balaji | A61B 5/7264 |
| 2018/0315193 | A1* | 11/2018 | Paschalakis | G06T 7/0016 |
| 2018/0368679 | A1* | 12/2018 | An | G06T 7/0012 |

FOREIGN PATENT DOCUMENTS

| | | |
|---|---|---|
| KR | 10-2013-0100384 A | 9/2013 |
| KR | 10-2014-0063288 A | 5/2014 |

OTHER PUBLICATIONS

Asiri, Norah, Muhammad Hussain, and Hatim A. Abualsamh. "Deep Learning based Computer-Aided Diagnosis Systems for Diabetic Retinopathy: A Survey." arXiv preprint arXiv:1811.01238 (2018). (Year: 2018).*

Alghamdi, Hanan S., et al. "Automatic optic disc abnormality detection in fundus images: A deep learning approach." (2016). (Year: 2016).*

Gondal, Waleed M., et al. "Weakly-supervised localization of diabetic retinopathy lesions in retinal fundus images." 2017 IEEE International Conference on Image Processing (ICIP). IEEE, 2017. (Year: 2017).*

PCT International Search Report, PCT Application No. PCT/KR2018/009809, dated Dec. 13, 2018, two pages.

* cited by examiner

DIAGNOSIS ASSISTANCE SYSTEM AND CONTROL METHOD THEREOF

CROSS-REFERENCE TO RELATED APPLICATION

This application is a continuation of PCT/KR2018/009809 filed on Aug. 24, 2018, which claims priority to Republic of Korea Patent Application No. 10-2017-0108232 filed on Aug. 25, 2017, which are incorporated by reference herein in their entirety.

TECHNICAL FIELD

The present invention relates to a diagnosis assistance system and control method thereof, and more particularly, to a diagnosis assistance system and control method thereof for providing diagnosis assistance information on the basis of an image.

BACKGROUND ART

The fundus examination is a diagnosis assistance material frequently utilized in ophthalmology since it is able to observe the abnormalities of the retina, optic nerve, and macula and allows the results to be confirmed by relatively simple imaging. In recent years, the fundus examination has been increasingly used because, through the fundus examination, it is able to observe not only eye diseases but also a degree of blood vessel damage caused by chronic diseases such as hypertension and diabetes by a non-invasive method.

Meanwhile, due to the recent rapid development of deep learning technology, the development of diagnostic artificial intelligence has been actively carried out in the field of medical diagnosis, especially the field of image-based diagnosis. Global companies such as Google and IBM have invested heavily in the development of artificial intelligence for analyzing a variety of medical video data, including large-scale data input through collaborations with the medical community. Some companies have succeeded in developing an artificial intelligence diagnostic tool that outputs superior diagnostic results.

However, in a case in which a plurality of values are desired to be predicted from a single test data through a deep learning trained model, there has been a problem in that accuracy of prediction is reduced and processing speed is lowered. Accordingly, there is a need for a system for learning and diagnosis that enables accurate prediction of a plurality of diagnostic characteristics at a high data processing speed.

SUMMARY

One object of the present invention is to provide a neural network model training method for acquiring diagnosis assistance information from a fundus image.

Another object of the present invention is to provide a method of training a plurality of neural network models in parallel to obtain a plurality of diagnosis assistance information from a fundus image.

Still another object of the present invention is to provide a method of promptly acquiring a plurality of diagnosis assistance information from a fundus image by using a machine learned neural network model.

Objects to be achieved by the present invention are not limited to those mentioned above, and other unmentioned objects should be clearly understood by one of ordinary skill in the art to which the present invention pertains from the present specification and the accompanying drawings.

According to an aspect of the present invention, there is provided a diagnosis assistance system for assisting diagnosis of a plurality of diseases based on a fundus image, the diagnosis assistance system including: a fundus image obtaining unit configured to obtain a target fundus image which is a basis for acquiring diagnosis assistance information on a subject; a first processing unit configured to, for the target fundus image, obtain a first result related to a first finding of the subject using a first neural network model, wherein the first neural network model is trained on the basis of a first fundus image set; a second processing unit configured to, for the target fundus image, obtain a second result related to a second finding of the subject using a second neural network model, wherein the second neural network model is trained on the basis of a second fundus image set which is at least partially different from the first fundus image set; a third processing unit configured to determine, on the basis of the first result and the second result, diagnostic information on the subject; and a diagnostic information output unit configured to provide the determined diagnostic information to a user. Here, the first finding and the second finding may be used for diagnosing different diseases.

According to another aspect of the present invention, there is provided a training device configured to obtain a first training data set including a plurality of fundus images, process a fundus image included in the first training data set, and train a first neural network model using the first training data set.

There is provided a control method of a training device, which is included in a system including a diagnostic device configured to obtain a target fundus image for obtaining diagnosis assistance information and obtain the diagnosis assistance information on the basis of the target fundus image by using a trained first neural network model, the control method including: pre-processing a first fundus image included in a first training data set so that the first fundus image is converted to a format facilitating the training of the first neural network model; serializing the pre-processed first fundus image; and training the first neural network model to classify, using the serialized first fundus image, the target fundus image to a first label or a second label.

Technical solutions of the present invention are not limited to those mentioned above, and other unmentioned technical solutions should be clearly understood by one of ordinary skill in the art to which the present invention pertains from the present specification and the accompanying drawings.

DETAILED DESCRIPTION OF EMBODIMENT

Figure 1:
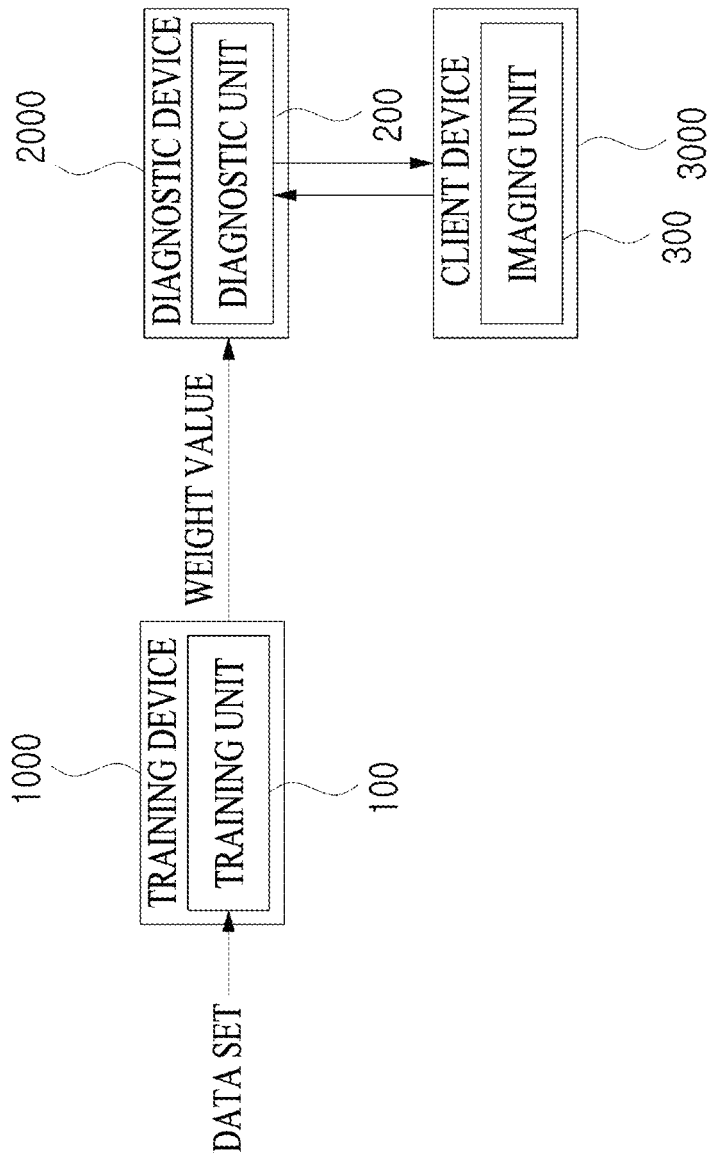
FIG. 1 illustrates a diagnosis assistance system according to an embodiment of the present invention.

The foregoing objects, features and advantages of the present invention will become more apparent from the following detailed description related to the accompanying drawings. It should be understood, however, that various modifications may be applied to the invention, and the invention may have various embodiments. Hereinafter, specific embodiments, which are illustrated in the drawings, will be described in detail.

In the drawings, the thicknesses of layers and regions are exaggerated for clarity. When it is indicated that an element or layer is "on" or "above" another element or layer, this includes a case in which another layer or element is interposed therebetween as well as a case in which the element or layer is directly above the other element or layer. In principle, like reference numerals designate like elements throughout the specification. In the following description, like reference numerals are used to designate elements which have the same function within the same idea illustrated in the drawings of each embodiment.

When detailed description of known functions or configurations related to the present invention is deemed to unnecessarily blur the gist of the invention, the detailed description thereof will be omitted. Also, numerals (e.g., first, second, etc.) used in the description herein are merely identifiers for distinguishing one element from another element.

In addition, the terms "module" and "unit" used to refer to elements in the following description are given or used in combination only in consideration of ease of writing the specification, and the terms themselves do not have distinct meanings or roles.

A method according to an embodiment may be implemented in the form of a program command that can be executed through various computer means and may be recorded in a computer-readable medium. The computer-readable medium may include program commands, data files, data structures, and the like alone or in combination. The program commands recorded in the medium may be those specially designed and configured for the embodiment or those known to those skilled in the art of computer software and usable. Examples of the computer-readable recording medium include magnetic media such as a hard disk, a floppy disk, and a magnetic tape, optical media such as compact disk-read only memory (CD-ROM), and a digital versatile disk (DVD), magneto-optical media such as a floptical disk, and hardware devices such as a read only memory (ROM), a random access memory (RAM), and a flash memory specially configured to store and execute a program command. Examples of the program command include high-level language codes that may be executed by a computer using an interpreter or the like as well as machine language codes generated by a compiler. The above-mentioned hardware device may be configured to operate as one or more software modules to execute operations according to an embodiment, and vice versa.

1. System and Process For Diagnosis Assistance 1.1 Purpose and Definition

Hereinafter, a system and method for diagnosis assistance for assisting in determination of the presence of a disease or illness on the basis of a fundus image or the presence of an abnormality which is a basis of the determination will be described. Particularly, a system or method for diagnosis assistance in which a neural network model for diagnosing a disease is constructed using a deep learning technique and detection of the presence of a disease or abnormal findings is assisted using the constructed model will be described.

According to an embodiment of the present invention, a system or method for diagnosis assistance in which diagnostic information related to the presence of a disease, findings information used in diagnosis of the presence of a disease, or the like are obtained on the basis of a fundus image and diagnosis is assisted using the obtained information may be provided.

According to an embodiment of the present invention, a system or method for diagnosis assistance in which diagnosis of an eye disease is assisted on the basis of a fundus image may be provided. For example, a system or method for diagnosis assistance in which diagnosis is assisted by obtaining diagnostic information related to the presence of glaucoma, cataract, macular degeneration, retinopathy of prematurity of a testee may be provided.

According to another embodiment of the present invention, a system or method for diagnosis assistance in which diagnosis of a disease other than an eye disease (for example, a systemic disease or a chronic disease) is assisted may be provided. For example, a system or method for diagnosis assistance in which diagnosis is assisted by obtaining diagnostic information on a systemic disease such as hypertension, diabetes, Alzheimer's, cytomegalovirus, stroke, heart disease, and arteriosclerosis may be provided.

According to still another embodiment of the present invention, a system or method for diagnosis assistance for detecting abnormal fundus findings that may be used in diagnosis of an eye disease or other diseases may be provided. For example, a system or method for diagnosis assistance for obtaining findings information such as abnormal color of the entire fundus, opacity of crystalline lens, abnormal cup-to-disc (C/D) ratio, macular abnormalities (e.g., macular hole), an abnormal diameter or course of a blood vessel, an abnormal diameter of the retinal artery, retinal hemorrhage, generation of exudate, and drusen may be provided.

In the specification, diagnosis assistance information may be understood as encompassing diagnostic information according to determination of the presence of a disease, findings information which is a basis of the determination, or the like.

1.2 Configuration of Diagnosis Assistance System

According to an embodiment of the present invention, a diagnosis assistance system may be provided.

FIG. 1 illustrates a diagnosis assistance system 10 according to an embodiment of the present invention. Referring to FIG. 1, the diagnosis assistance system 10 may include a training device 1000 configured to train a diagnostic model, a diagnostic device 2000 configured to perform diagnosis using the diagnostic model, and a client device 3000 configured to obtain a diagnosis request. The diagnosis assistance system 10 may include a plurality of training devices, a plurality of diagnostic devices, or a plurality of client devices.

The training device 1000 may include a training unit 100. The training unit 100 may perform training of a neural network model. For example, the training unit 100 may obtain a fundus image data set and perform training of a neural network model that detects a disease or abnormal findings from a fundus image.

The diagnostic device 2000 may include a diagnostic unit 200. The diagnostic unit 200 may perform diagnosis of a disease or obtain assistance information used for the diagnosis by using a neural network model. For example, the diagnostic unit 200 may obtain diagnosis assistance information by using a diagnostic model trained by the training unit.

The client device 3000 may include an imaging unit 300. The imaging unit 300 may capture a fundus image. The client device may be an ophthalmic fundus imaging device. Alternatively, the client device 3000 may be a handheld device such as a smartphone or a tablet personal computer (PC).

In the diagnosis assistance system 10 according to the present embodiment, the training device 1000 may obtain a data set and train a neural network model to determine a neural network model to be used in diagnosis assistance, the diagnostic device may obtain diagnosis assistance information according to a diagnosis target image by using the determined neural network model when an information request is obtained from the client device, and the client device may request the diagnostic device for information and obtain diagnosis assistance information transmitted in response to the request.

A diagnosis assistance system according to another embodiment may include a diagnostic device configured to train a diagnostic model and perform diagnosis using the same and may include a client device. A diagnosis assistance system according to still another embodiment may include a diagnostic device configured to train a diagnostic model, obtain a diagnosis request, and perform diagnosis. A diagnosis assistance system according to yet another embodiment may include a training device configured to train a diagnostic model and a diagnostic device configured to obtain a diagnosis request and perform diagnosis.

The diagnosis assistance system disclosed herein is not limited to the above-described embodiments and may be implemented in any form including a training unit configured to train a model, a diagnostic unit configured to obtain diagnosis assistance information according to the trained image, and an imaging unit configured to obtain a diagnosis target image.

Hereinafter, some embodiments of each device constituting the system will be described.

1.2.1 Training Device

A training device according to an embodiment of the present invention may train a neural network model that assists diagnosis.

Figure 2:
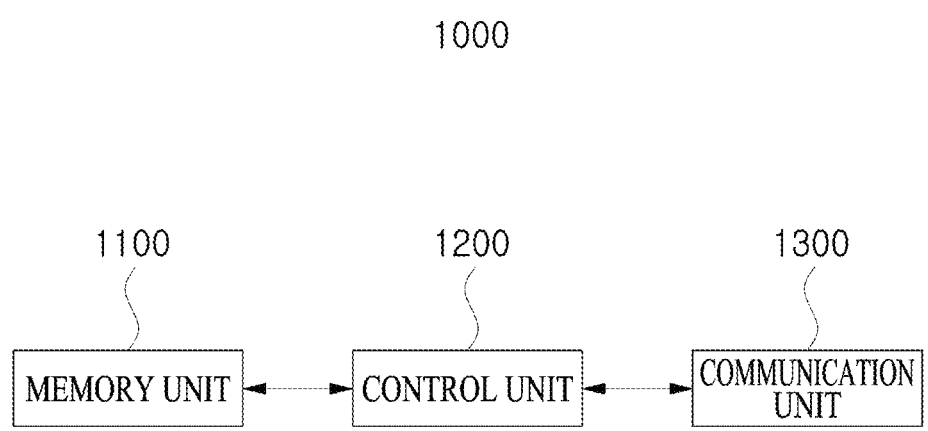
FIG. 2 is a block diagram for describing a training device according to an embodiment of the present invention.

FIG. 2 is a block diagram for describing a training device 1000 according to an embodiment of the present invention. Referring to FIG. 2, the training device 1000 may include a control unit 1200 and a memory unit 1100.

The training device 1000 may include the control unit 1200. The control unit 1200 may control operation of the training device 1000.

The control unit 1200 may include one or more of a central processing unit (CPU), a random access memory (RAM), a graphic processing unit (GPU), one or more microprocessors, and an electronic component capable of processing input data according to predetermined logic.

The control unit 1200 may read a system program and various processing programs stored in the memory unit 1100. For example, the control unit 1200 may develop a data processing process for performing diagnosis assistance which will be described below, a diagnostic process, and the like in a RAM and perform various processes according to a developed program. The control unit 1200 may perform training of a neural network model which will be described below.

The training device 1000 may include the memory unit 1100. The memory unit 1100 may store data required for training and a training model.

The memory unit 1100 may be implemented using a nonvolatile semiconductor memory, a hard disk, a flash memory, a RAM, a ROM, an electrically erasable programmable ROM (EEPROM), or other tangible nonvolatile recording media.

The memory unit 1100 may store various processing programs, parameters for processing programs, result data of such processing, or the like. For example, the memory unit 1100 may store a data processing process program for performing diagnosis assistance which will be described below, a diagnostic process program, parameters for executing each program, data obtained according to execution of such programs (for example, processed data or diagnosis result values), and the like.

The training device 1000 may include a separate training unit (or training module). The training unit may train a neural network model. The training will be described in more detail below in Section "2. Training process."

The training unit may be included in the above-described control unit 1200. The training unit may be stored in the above-described memory unit 1100. The training unit may be implemented by partial configurations of the above-described control unit 1200 and memory unit 1100. For example, the training unit may be stored in the memory unit 1100 and driven by the control unit 1200.

The training device 1000 may further include a communication unit 1300. The communication unit 1300 may communicate with an external device. For example, the communication unit 1300 may communicate with a diagnostic device, a server device, or a client device which will be described below. The communication unit 1300 may perform wired or wireless communication. The communication unit 1300 may perform bidirectional or unidirectional communication.

Figure 3:
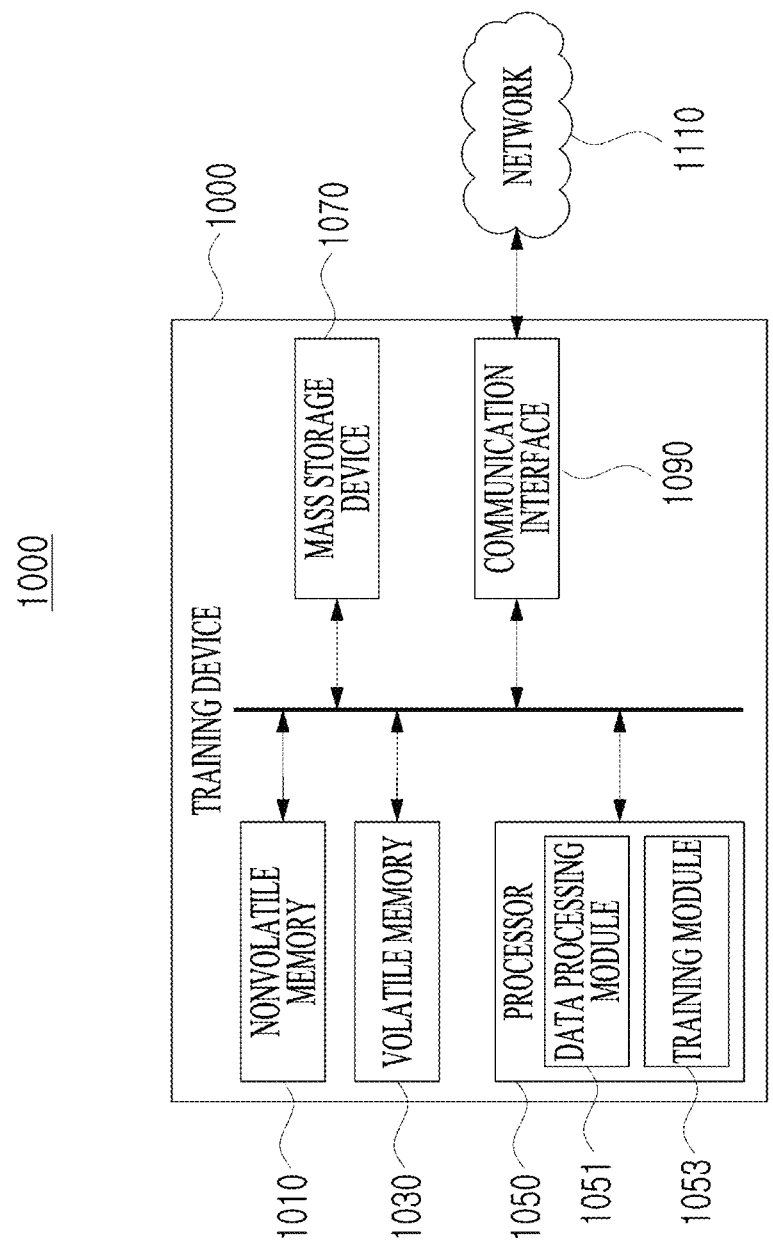
FIG. 3 is a block diagram for describing the training device in more detail according to another embodiment of the present invention.

FIG. 3 is a block diagram for describing the training device 1000 in more detail according to another embodiment of the present invention. Referring to FIG. 3, the training device 1000 may include a processor 1050, a volatile memory 1030, a nonvolatile memory 1010, a mass storage device 1070, and a communication interface 1090.

The processor 1050 of the training device 1000 may include a data processing module 1051 and a training module 1053. The processor 1050 may process a data set stored in the mass storage device or nonvolatile memory through the data processing module 1051. The processor 1050 may train a diagnosis assistance neural network model through the training module 1053. The processor 1050 may include a local memory. The communication interface 1090 may be connected to a network 1110.

However, the training device 1000 illustrated in FIG. 3 is merely an example, and the configuration of the training device 1000 according to the present invention is not limited thereto. Particularly, the data processing module or training module may be provided at locations different from those illustrated in FIG. 3.

1.2.2 Diagnostic Device

A diagnostic device may obtain diagnosis assistance information using a neural network model.

Figure 4:
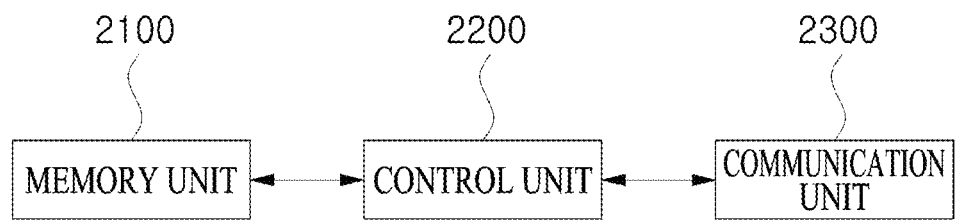
FIG. 4 is a block diagram for describing a diagnostic device according to an embodiment of the present invention.

FIG. 4 is a block diagram for describing a diagnostic device 2000 according to an embodiment of the present invention. Referring to FIG. 4, the diagnostic device 2000 may include a control unit 2200 and a memory unit 2100.

The control unit 2200 may generate diagnosis assistance information using a diagnosis assistance neural network model. The control unit 2200 may obtain diagnostic data for diagnosis (for example, fundus data of a testee) and obtain diagnosis assistance information predicted by the diagnostic data using a trained diagnosis assistance neural network model.

The memory unit 2100 may store a trained diagnosis assistance neural network model. The memory unit 2100 may store parameters, variables, and the like of a diagnosis assistance neural network model.

The diagnostic device 2000 may further include a communication unit 2300. The communication unit 2300 may communicate with a training device and/or a client device. For example, the diagnostic device 2000 may be provided in the form of a server that communicates with a client device. This will be described in more detail below.

Figure 5:
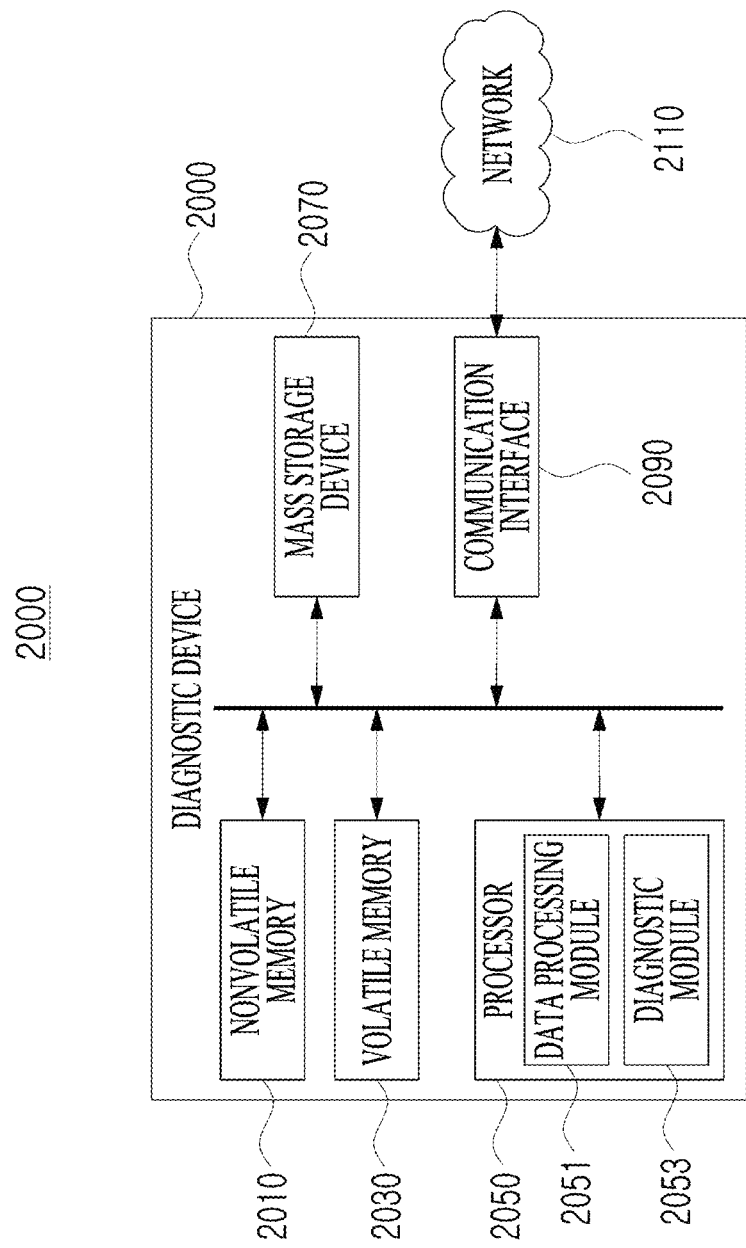
FIG. 5 is a view for describing the diagnostic device according to another embodiment of the present invention.

FIG. 5 is a view for describing the diagnostic device 2000 according to another embodiment of the present invention. Referring to FIG. 5, the diagnostic device 2000 according to an embodiment of the present invention may include a processor 2050, a volatile memory 2030, a nonvolatile memory 2010, a mass storage device 2070, and a communication interface 2090.

The processor 2050 of the diagnostic device may include a data processing module 2051 and a diagnostic module 2053. The processor 2050 may process diagnostic data through the data processing module 2051 and obtain diagnosis assistance information according to the diagnostic data through the diagnostic module 2053.

1.2.3 Server Device

According to an embodiment of the present invention, a diagnosis assistance system may include a server device. The diagnosis assistance system according to an embodiment of the present invention may also include a plurality of server devices.

The server device may store and/or drive a neural network model. The server device may store weights constituting a trained neural network model. The server device may collect or store data used in diagnosis assistance.

The server device may output a result of a diagnosis assistance process using a neural network model to a client device. The server device may obtain feedback from the client device. The server device may operate similar to the above-described diagnostic device.

Figure 6:
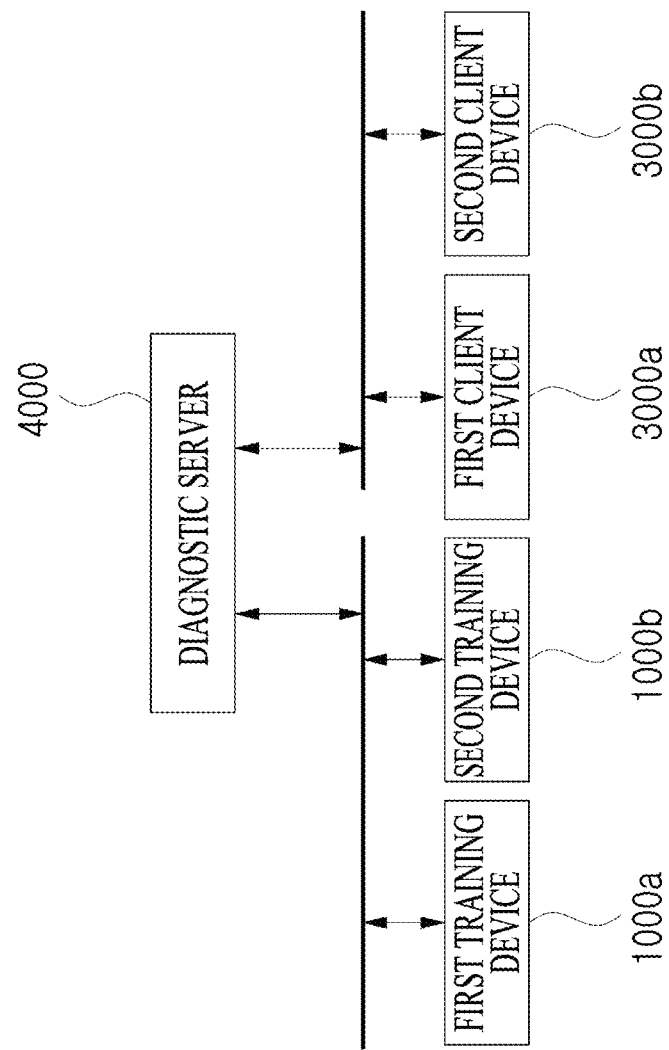
FIG. 6 illustrates a diagnosis assistance system according to an embodiment of the present invention.

FIG. 6 illustrates a diagnosis assistance system 20 according to an embodiment of the present invention. Referring to FIG. 6, the diagnosis assistance system 20 according to an embodiment of the present invention may include a diagnostic server 4000, a training device, and a client device.

The diagnostic server 4000, i.e., server device, may communicate with a plurality of training devices or a plurality of diagnostic devices. Referring to FIG. 6, the diagnostic server 4000 may communicate with a first training device 1000*a* and a second training device 1000*b*. Referring to FIG. 6, the diagnostic server 4000 may communicate with a first client device 3000*a* and a second client device 3000*b*.

For example, the diagnostic server 4000 may communicate with the first training device 1000*a* configured to train a first diagnosis assistance neural network model that obtains a first diagnosis assistance information and the second training device 1000*b* configured to train a second diagnosis assistance neural network model that obtains a second diagnosis assistance information.

The diagnostic server 4000 may store the first diagnosis assistance neural network model that obtains the first diagnosis assistance information and the second diagnosis assistance neural network model that obtains the second diagnosis assistance information, obtain diagnosis assistance information in response to a request for obtaining diagnosis assistance information from the first client device 3000a or the second client device 3000b, and transmit the obtained diagnosis assistance information to the first client device 3000a or the second client device 3000b.

Alternatively, the diagnostic server 4000 may communicate with the first client device 3000a that requests for the first diagnosis assistance information and the second client device 3000b that requests for the second diagnosis assistance information.

1.2.4 Client Device

A client device may request a diagnostic device or a server device for diagnosis assistance information. The client device may obtain data required for diagnosis and transmit the obtained data to the diagnostic device.

The client device may include a data obtaining unit. The data obtaining unit may obtain data required for diagnosis assistance. The data obtaining unit may be an imaging unit configured to obtain an image used in a diagnosis assistance model.

Figure 7:
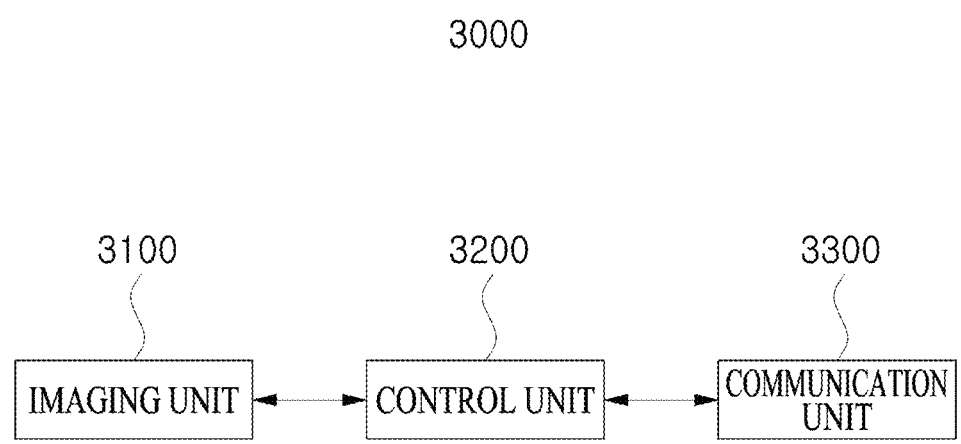
FIG. 7 is a block diagram for describing a client device according to an embodiment of the present invention.

FIG. 7 is a block diagram for describing the client device 3000 according to an embodiment of the present invention. Referring to FIG. 7, the client device 3000 according to an embodiment of the present invention may include an imaging unit 3100, a control unit 3200, and a communication unit 3300.

The imaging unit 3100 may obtain image or video data. The imaging unit 3100 may obtain a fundus image. However, in the client device 3000, the imaging unit 3100 may also be substituted with another form of data obtaining unit.

The communication unit 3300 may communicate with an external device, e.g., a diagnostic device or a server device. The communication unit 3300 may perform wired or wireless communication.

The control unit 3200 may control the imaging unit 3100 to obtain images or data. The control unit 3200 may control the imaging unit 3100 to obtain a fundus image. The control unit 3200 may transmit the obtained fundus image to the diagnostic device. The control unit may transmit an image obtained through the imaging unit 3100 to the server device through the communication unit 3300 and obtain diagnosis assistance information generated on the basis of the obtained image.

Although not illustrated, the client device may further include an output unit. The output unit may include a display configured to output a video or an image or may include a speaker configured to output sound. The output unit may output video or image data obtained by the imaging unit. The output unit may output diagnosis assistance information obtained from the diagnostic device.

Although not illustrated, the client device may further include an input unit. The input unit may obtain a user input. For example, the input unit may obtain a user input that requests for diagnosis assistance information. The input unit may obtain information on a user who evaluates diagnosis assistance information obtained from the diagnostic device.

In addition, although not illustrated, the client device may further include a memory unit. The memory unit may store an image obtained by the imaging unit.

1.3 Outline of Diagnosis Assistance Process

A diagnosis assistance process may be performed by a diagnosis assistance system or a diagnosis assistance device disclosed herein. The diagnosis assistance process may be taken into consideration by being mainly divided into a training process for training a diagnosis assistance model used in diagnosis assistance and a diagnostic process using the diagnosis assistance model.

Figure 8:
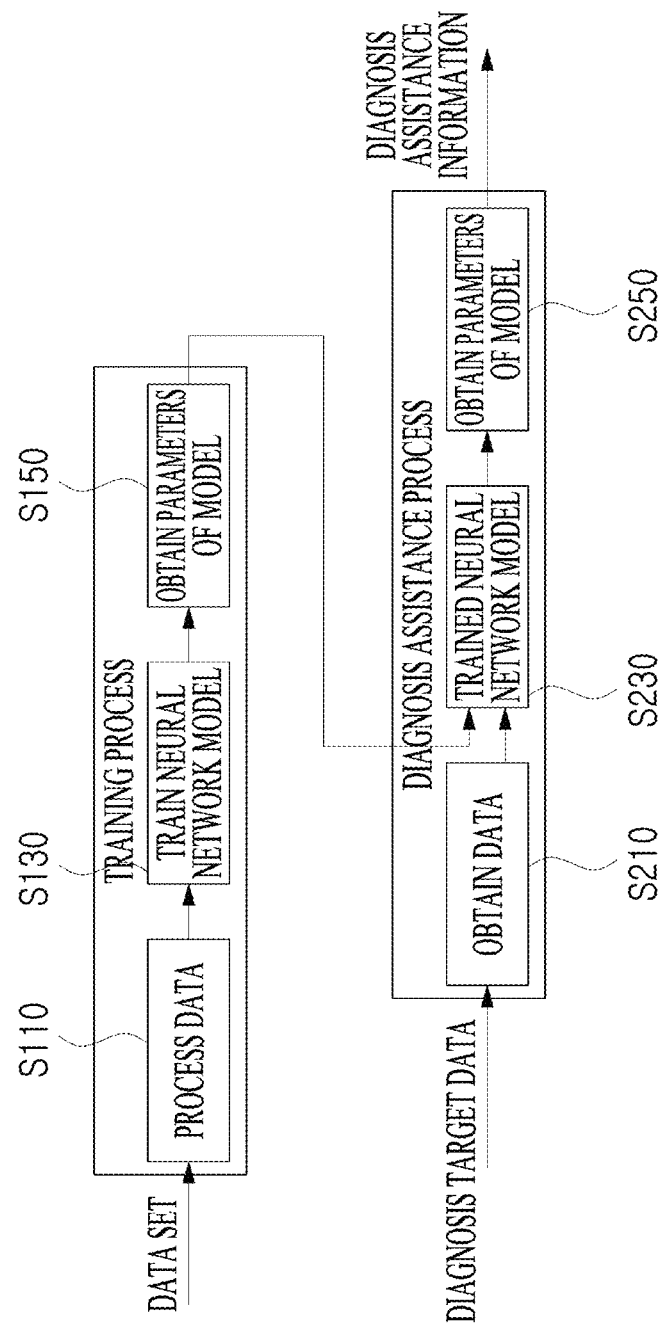
FIG. 8 is a view for describing a diagnosis assistance process according to an embodiment of the present invention.

FIG. 8 is a view for describing a diagnosis assistance process according to an embodiment of the present invention. Referring to FIG. 8, the diagnosis assistance process according to an embodiment of the present invention may include a training process including obtaining and processing data (S110), training a neural network model (S130), and obtaining variables of the trained neural network model (S150) and a diagnosis assistance process including obtaining diagnosis target data (S210), using a neural network model trained on the basis of the diagnosis target data (S230), and obtaining diagnosis assistance information using the trained neural network model (S250).

More specifically, the training process may include a data processing process in which input training image data is processed to a state in which the data may be used for model training and a training process in which a model is trained using the processed data. The training process may be performed by the above-described training device.

The diagnostic process may include a data processing process in which input examination target image data is processed to a state in which diagnosis using a neural network model may be performed and a diagnostic process in which diagnosis is performed using the processed data. The diagnostic process may be performed by the above-described diagnostic device or server device.

Hereinafter, each process will be described.

2. Training Process

According to an embodiment of the present invention, a process for training a neural network model may be provided. As a specific example, a process for training a neural network model that performs or assists diagnosis on the basis of a fundus image may be disclosed.

The training process which will be described below may be performed by the above-described training device.

2.1 Training Unit

According to an embodiment of the present invention, a training process may be performed by a training unit. The training unit may be provided in the above-described training device.

Figure 9:
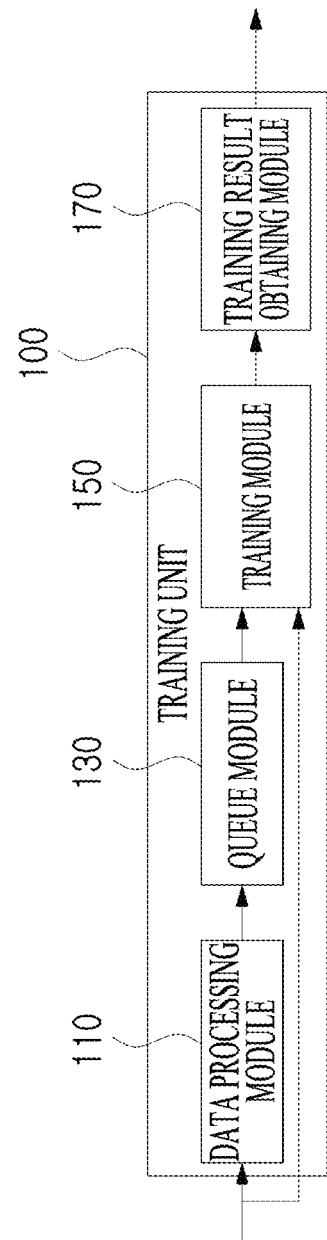
FIG. 9 is a view for describing a configuration of a training unit according to an embodiment of the present invention.

FIG. 9 is a view for describing a configuration of a training unit 100 according to an embodiment of the present invention. Referring to FIG. 9, the training unit 100 may include a data processing module 110, a queue module 130, a training module 150, and a training result obtaining module 170. As will be described below, the modules may perform individual steps of a data processing process and a training process. However, not all of the elements described with reference to FIG. 9 and functions performed by the elements are essential, and some elements may be added or omitted according to a form of training.

2.2 Data Processing Process 2.2.1 Obtaining Image Data

According to an embodiment of the present invention, a data set may be obtained. According to an embodiment of the present invention, a data processing module may obtain a data set.

The data set may be an image data set. Specifically, the data set may be a fundus image data set. The fundus image data set may be obtained using a general non-mydriatic fundus camera or the like. A fundus image may be a panorama image. The fundus image may be a red-free image. The fundus image may be an infrared image. The fundus image may be an autofluorescence image. The image data may be obtained in any one format among JPG, PNG, DCM (DICOM), BMP, GIF, and TIFF.

The data set may include a training data set. The data set may include a test data set. The data set may include a validation data set. In other words, the data set may be assigned as at least one of a training data set, a test data set, and a validation data set.

The data set may be determined in consideration of diagnosis assistance information that is desired to be obtained using a neural network model trained through the corresponding data set. For example, when it is desired to train a neural network model that obtains diagnosis assistance information related to cataract, an infrared fundus image data set may be determined as a data set to be obtained. Alternatively, when it is desired to train a neural network model that obtains diagnosis assistance information related to macular degeneration, an obtained data set may be an autofluorescence fundus image data set.

Individual data included in a data set may include a label. There may be a plurality of labels. In other words, individual data included in a data set may be labeled in relation to at least one feature. For example, a data set may be a fundus image data set including a plurality of fundus image data, and each fundus image data may include a label related to diagnostic information (for example, the presence of a specific disease) and/or a label related to findings information (for example, whether a specific site is abnormal) according to the corresponding image.

As another example, a data set may be a fundus image data set, and each fundus image data may include a label related to peripheral information on the corresponding image. For example, each fundus image data may include a label related to peripheral information including left eye/right eye information on whether the corresponding fundus image is an image of the left eye or an image of the right eye, gender information on whether the corresponding fundus image is a fundus image of a female or a fundus image of a male, age information on the age of a testee to which the corresponding fundus image belongs, and the like.

Figure 10:
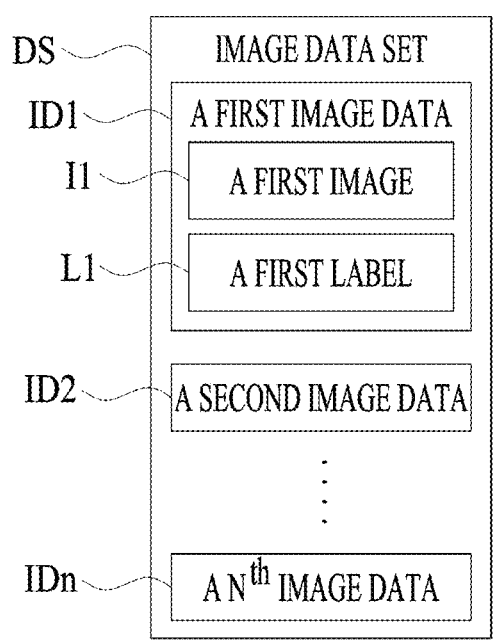
FIG. 10 is a conceptual diagram for describing an image data set according to an embodiment of the present invention.

FIG. 10 is a conceptual diagram for describing an image data set DS according to an embodiment of the present invention. Referring to FIG. 10, the image data set DS according to an embodiment of the present invention may include a plurality of image data ID. Each image data ID may include an image I and a label L assigned to the image. Referring to FIG. 10, the image data set DS may include a first image data ID1 and a second image data ID2. The first image data ID1 may include a first image I1 and a first label L1 corresponding to the first image.

Although the case in which a single image data includes a single label has been described above with reference to FIG. 10, a single image data may include a plurality of labels as described above.

2.2.2 Image Resizing

According to an embodiment of the present invention, the size of an obtained piece of image data may be adjusted. That is, images may be resized. According to an embodiment of the present invention, image resizing may be performed by the data processing module of the above-described training unit.

The size or aspect ratio of an image may be adjusted. Sizes of a plurality of obtained images may be adjusted so that the images have a certain size. Alternatively, the sizes of the images may be adjusted so that the images have a certain aspect ratio. Resizing an image may include applying an image conversion filter to an image.

When the sizes or capacities of obtained individual images are excessively large or small, the size or volume of an image may be adjusted to convert the image to an appropriate size. Alternatively, when the sizes or capacities of individual images vary, the sizes or capacities may be made uniform through resizing.

According to an embodiment, a volume of an image may be adjusted. For example, when a volume of an image exceeds an appropriate range, the image may be reduced through down-sampling. Alternatively, when a volume of an image is below an appropriate range, the image may be enlarged through up-sampling or interpolating.

According to another embodiment, an image may be cut or pixels may be added to an obtained image to adjust the size or aspect ratio of the image. For example, when a portion unnecessary for training is included in an image, a portion of the image may be cropped to remove the unnecessary portion. Alternatively, when a portion of the image is cut away and a set aspect ratio is not met, a column or row may be added to the image to adjust the aspect ratio of the image. In other words, a margin or padding may be added to the image to adjust the aspect ratio.

According to still another embodiment, the volume and the size or aspect ratio of the image may be adjusted together. For example, when a volume of an image is large, the image may be down-sampled to reduce the volume of the image, and an unnecessary portion included in the reduced image may be cropped to convert the image to appropriate image data.

According to another embodiment of the present invention, an orientation of image data may be changed.

As a specific example, when a fundus image data set is used as a data set, the volume or size of each fundus image may be adjusted. Cropping may be performed to remove a margin portion excluding a fundus portion of a fundus image, or padding may be performed to supplement a cut-away portion of a fundus image and adjust an aspect ratio thereof.

Figure 11:
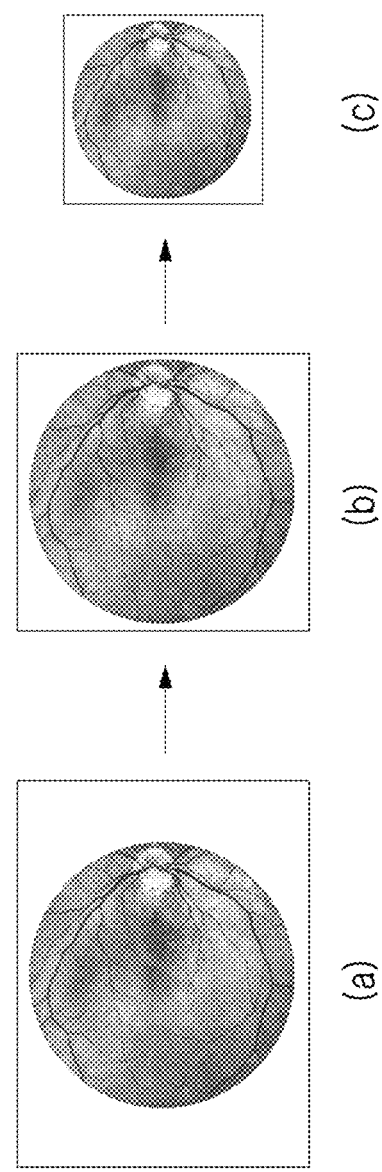
FIG. 11 is a view for describing image resizing according to an embodiment of the present invention.

FIG. 11 is a view for describing image resizing according to an embodiment of the present invention. Referring to FIG. 11, an obtained fundus image may be resized by an image resizing process according to an embodiment of the present invention.

Specifically, an original fundus image (a) may be cropped as shown in (b) so that a margin portion unnecessary for obtaining diagnostic information is removed or the size thereof may be reduced as shown in (c) for enhancing the training efficiency.

2.2.3 Image Pre-processing

According to an embodiment of the present invention, image pre-processing may be performed. When an input image is used as it is in training, an overfitting phenomenon may occur as a result of a training for unnecessary characteristics, and the training efficiency may also be degraded.

To prevent this, image data may be appropriately pre-processed to serve a purpose of training, thereby improving the efficiency and performance of training. For example, pre-processing of a fundus image may be performed to facilitate detection of abnormal symptoms of an eye disease, or pre-processing of a fundus image may be performed so that changes in retinal vessels or blood flow are emphasized.

Image pre-processing may be performed by the data processing module of the above-described training unit. The data processing module may obtain a resized image and perform pre-processing required for training.

Image pre-processing may be performed on the above-mentioned resized image. However, content of the invention disclosed herein is not limited thereto, and image pre-processing may also be performed without the resizing process. Pre-processing an image may include applying a pre-processing filter to the image.

According to an embodiment, a blur filter may be applied to an image. A Gaussian filter may be applied to an image. A Gaussian blur filter may also be applied to an image. Alternatively, a deblur filter which sharpens an image may be applied to the image.

According to another embodiment, a filter that adjusts or modulates color of an image may be applied. For example, a filter that changes values of some components of RGB values constituting an image or binarizes the image may be applied.

According to still another embodiment, a filter that causes a specific element in an image to be emphasized may be applied to the image. For example, pre-processing that causes a blood vessel element to be emphasized from each image may be performed on fundus image data. In this case, the pre-processing that causes a blood vessel element to be emphasized may include applying one or more filters sequentially or in combination.

According to an embodiment of the present invention, image pre-processing may be performed in consideration of a characteristic of diagnosis assistance information that is desired to be obtained. For example, when it is desired to obtain diagnosis assistance information related to findings such as retinal hemorrhage, drusen, microaneurysms, and exudates, pre-processing that converts an obtained fundus image into a red-free fundus image may be performed.

2.2.4 Image Augmentation

According to an embodiment of the present invention, an image may be augmented or expanded. Image augmentation may be performed by the data processing module of the above-described training unit.

Augmented images may be used for improving performance of training a neural network model. For example, when an amount of data for training a neural network model is insufficient, existing training image data may be modulated to increase the number of data for training, and modulated (or modified) images may be used together with an original image, thereby increasing the number of training image data. Accordingly, overfitting may be suppressed, layers of a model may be formed deeper, and accuracy of prediction may be improved.

For example, expansion of image data may be performed by reversing the left and right of an image, cutting (cropping) a part of the image, correcting a color value of the image, or adding artificial noise to the image. As a specific example, cutting a part of the image may be performed by cutting a partial region of an element constituting an image or randomly cutting partial regions. In addition, image data may be expanded by reversing the left and right of the image data, reversing the top and bottom of the image data, rotating the image data, resizing the image data to a certain ratio, cropping the image data, padding the image data, adjusting color of the image data, or adjusting brightness of the image data.

For example, the above-described augmentation or expansion of image data may be generally applied to a training data set. However, the augmentation or expansion of image data may also be applied to other data sets, for example, a test data set, i.e., a data set for testing a model on which training using training data and validation using validation data have been completed.

As a specific example, when a fundus image data set is used as a data set, an augmented fundus image data set may be obtained by randomly applying one or more processes of reversing an image, cutting an image, adding noise to an image, and changing color of an image to increase the number of data.

Figure 12:
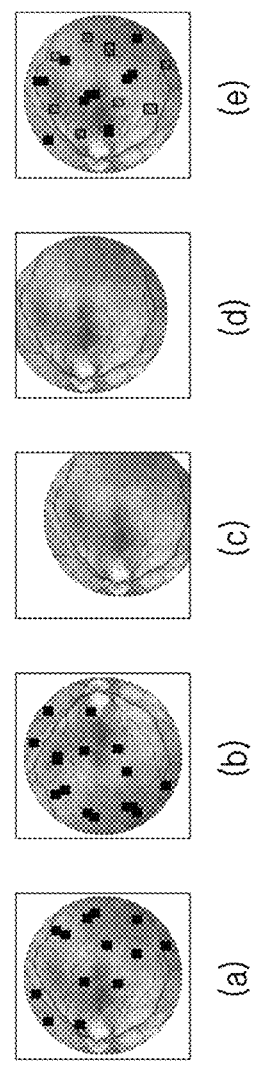
FIG. 12 is a view for describing expansion of an image data set according to an embodiment of the present invention.

FIG. 12 is a view for describing expansion of an image data set according to an embodiment of the present invention. Referring to FIG. 12, an image according to embodiments of the present invention may be deformed to improve prediction accuracy of a neural network model.

Specifically, referring to FIG. 12, partial regions may be dropped out from an image according to embodiments of the present invention as shown in (a), the left and right of the image may be reversed as shown in (b), a central point of the image may be moved as shown in (c) and (d), and color of partial regions of the image may be modulated as shown in (e).

2.2.5 Image Serialization

According to an embodiment of the present invention, image data may be serialized. An image may be serialized by the data processing module of the above-described training unit. A serializing module may serialize pre-processed image data and transmit the serialized image data to a queue module.

When image data is used as it is in training, since the image data has an image file format such as JPG, PNG, and DCM, decoding is necessary. However, when training is performed through decoding every time, performance of training a model may be degraded. Accordingly, training may be performed using an serialized image instead of using the image file as it is in training. Therefore, image data may be serialized to improve the performance and speed of training. The image data being serialized may be image data to which one or more steps of the above-described image resizing and image pre-processing are applied or may be image data on which neither the image resizing nor the image pre-processing has been processed.

Each piece of image data included in an image data set may be converted to a string format. Image data may be converted to a binarized data format. Particularly, image data may be converted to a data format suitable for use in training a neural network model. For example, image data may be converted to the TFRecord format for use in training a neural network model using Tensorflow.

As a specific example, when a fundus image set is used as a data set, the obtained fundus image set may be converted to the TFRecord format and used in training a neural network model.

2.2.6 Queue

A queue may be used for solving a data bottleneck phenomenon. The queue module of the above-described training unit may store image data in a queue and transmit the image data to a training module.

Particularly, when a training process is performed by using a CPU and a GPU together, a bottleneck phenomenon between the CPU and the GPU may be minimized, access to a database may be facilitated, and the memory usage efficiency may be enhanced by using a queue.

A queue may store data used in training a neural network model. The queue may store image data. The image data stored in the queue may be image data on which at least one of the above-described data processing processes (that is, resizing, pre-processing, and augmentation) are processed or may be image data that is unchanged after being obtained.

A queue may store image data, preferably, serialized image data as described above. The queue may store image data and supply the image data to a neural network model. The queue may transfer image data in batch size to a neural network model.

A queue may provide image data. The queue may provide data to a training module which will be described below. As data is extracted from the training module, the number of data accumulated in the queue may be decreased.

When the number of data stored in the queue is decreased to a reference number or lower as training of a neural network model is performed, the queue may request for supplementation of data. The queue may request for supplementation of a specific type of data. When the queue requests the training unit for supplementation of data, the training unit may supplement the queue with data.

A queue may be provided in a system memory of the training device. For example, the queue may be formed in a RAM of a CPU. In this case, the size, i.e., volume, of the queue may be set according to the capacity of the RAM of the CPU. A first-in-first-out (FIFO) queue, a primary queue, or a random queue may be used as the queue.

2.3 Training Process

According to an embodiment of the present invention, a training process of a neural network model may be disclosed.

According to an embodiment of the present invention, training of a neural network model may be performed by the above-described training device. A training process may be performed by the control unit of the training device. A training process may be performed by the training module of the above-described training unit.

Figure 13:
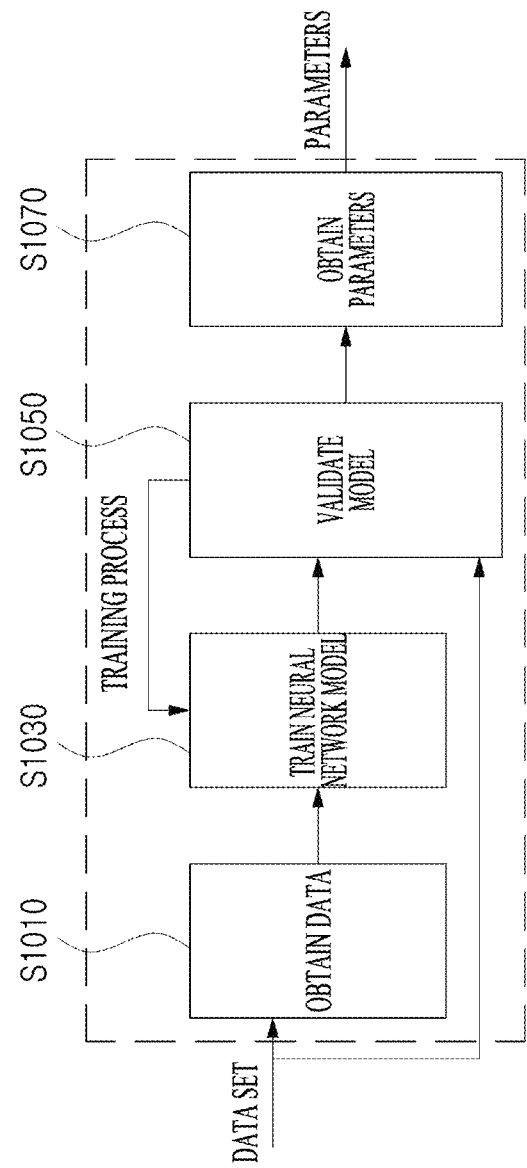
FIG. 13 is a block diagram for describing a training process of a neural network model according to an embodiment of the present invention.

FIG. 13 is a block diagram for describing a training process of a neural network model according to an embodiment of the present invention. Referring to FIG. 13, a training process of a neural network model according to an embodiment of the present invention may be performed by obtaining data (S1010), training a neural network model (S1030), validating the trained model (S1050), and obtaining variables of the trained model (S1070).

Hereinafter, some embodiments of a training process of a neural network model will be described with reference to FIG. 13.

2.3.1 Data Input

A data set for training a diagnosis assistance neural network model may be obtained.

Obtained data may be an image data set processed by the above-described data processing process. For example, a data set may include fundus image data which is adjusted in size, has a pre-processing filter applied thereto, is augmented and then serialized.

In training a neural network model, a training data set may be obtained and used. In validating the neural network model, a validation data set may be obtained and used. In testing the neural network model, a test data set may be obtained and used. Each data set may include fundus images and labels.

A data set may be obtained from a queue. The data set may be obtained in batches from the queue. For example, when sixty data sets are designated as the size of a batch, sixty data sets may be extracted at a time from the queue. The size of a batch may be limited by the capacity of a RAM of a GPU.

A data set may be randomly obtained from a queue by the training module. Data sets may also be obtained in order of being accumulated in the queue.

The training module may extract a data set by designating a configuration of a data set to be obtained from the queue. For example, the training module may extract fundus image data having a left eye label of a specific patient and fundus image data having a right eye label of the specific patient to be used together in training.

The training module may obtain a data set having a specific label from the queue. For example, the training module may obtain fundus image data in which a diagnostic information label is abnormal label from the queue. The training module may obtain a data set from the queue by designating a ratio between numbers of data according to certain labels. For example, the training module may obtain a fundus image data set from the queue so that the number of fundus image data in which a diagnostic information label is abnormal and the number of fundus image data in which the diagnostic information label is normal has a 1:1 ratio.

2.3.2 Model Design

A neural network model may be a diagnosis assistance model that outputs diagnosis assistance information on the basis of image data. A structure of a diagnosis assistance neural network model for obtaining diagnosis assistance information may have a predetermined form. The neural network model may include a plurality of layers.

A neural network model may be implemented in the form of a classifier that generates diagnosis assistance information. The classifier may perform binary classification or multiclass classification. For example, a neural network model may be a binary classification model that classifies input data as a normal or abnormal class in relation to target diagnosis assistance information such as a specific disease or abnormal symptoms. Alternatively, a neural network model may be a multiclass classification model that classifies input data into a plurality of classes in relation to a specific characteristic (for example, a degree of disease progression). Alternatively, a neural network model may be implemented as a regression model that outputs specific values related to a specific disease.

A neural network model may include a convolutional neural network (CNN). As a CNN structure, at least one of AlexNet, LENET, NIN, VGGNet, ResNet, WideResnet, GoogleNet, FractaNet, DenseNet, FitNet, RitResNet, HighwayNet, MobileNet, and DeeplySupervisedNet may be used. The neural network model may be implemented using a plurality of CNN structures.

For example, a neural network model may be implemented to include a plurality of VGGNet blocks. As a more specific example, a neural network model may be provided by coupling between a first structure in which a 3×3 CNN layer having 64 filters, a batch normalization (BN) layer, and a ReLu layer are sequentially coupled and a second block in which a 3×3 CNN layer having 128 filters, a ReLu layer, and a BN layer are sequentially coupled.

A neural network model may include a max pooling layer subsequent to each CNN block and include a global average pooling (GAP) layer, a fully connected (FC) layer, and an activation layer (for example, sigmoid, softmax, and the like) at an end.

2.3.3 Model Training

A neural network model may be trained using a training data set.

A neural network model may be trained using a labeled data set. However, a training process of a diagnosis assistance neural network model described herein is not limited thereto, and a neural network model may also be trained in an unsupervised form using unlabeled data.

Training of a neural network model may be performed by obtaining a result value using a neural network model to which arbitrary weights are assigned on the basis of training image data, comparing the obtained result value with a label value of the training data, and performing backpropagation according to an error therebetween to optimize the weights. Also, training of a neural network model may be affected by a result of validating the model, a result of testing the model, and/or feedback on the model received from the diagnosis step.

The above-described training of a neural network model may be performed using Tensorflow. However, the present invention is not limited thereto, and a framework such as Theano, Keras, Caffe, Torch, and Microsoft Cognitive Toolkit (CNTK) may also be used in training a neural network model.

2.3.4 Model Validation

A neural network model may be validated using a validation data set. Validation of a neural network model may be performed by obtaining a result value related to a validation data set from a neural network model which has been trained and comparing the result value with a label of the validation data set. The validation may be performed by measuring accuracy of the result value. Parameters of a neural network model (for example, weights and/or bias) or hyperparameters (for example, learning rate) of the neural network model may be adjusted according to a validation result.

For example, the training device according to an embodiment of the present invention may train a neural network model that predicts diagnosis assistance information on the basis of a fundus image and compare diagnosis assistance information on a validated fundus image of the trained model with a validation label corresponding to the validated fundus image to perform validation of the diagnosis assistance neural network model.

In validation of a neural network model, an external data set, that is, a data set having a distinguished factor not included in a training data set, may be used. For example, the external data set may be a data set in which factors such as race, environment, age, and gender are distinguished from the training data set.

2.3.5 Model Test

A neural network model may be tested using a test data set.

Although not illustrated in FIG. 13, according to the training process according to an embodiment of the present invention, a neural network model may be tested using a test data set which is differentiated from a training data set and a validation data set. Parameters of a neural network model (for example, weights and/or bias) or hyperparameters (for example, learning rate) of the neural network model may be adjusted according to a test result.

For example, the training device according to an embodiment of the present invention may obtain a result value which has test fundus image data, which has not been used in the training and validation, as input from the neural network model which has been trained to predict diagnosis assistance information on the basis of a fundus image and may perform testing of the diagnosis assistance neural network model which has been trained and validated.

In testing of the neural network model, an external data set, that is, a data set having a factor distinguished from the training data set and/or validation data set, may be used.

2.3.6 Output of Result

As a result of training a neural network model, optimized parameter values of the model may be obtained. As training of the model using a test data set as described above is repeatedly performed, more appropriate parameter (variable) values may be obtained. When the training is sufficiently performed, optimized values of weights and/or bias may be obtained.

According to an embodiment of the present invention, a trained neural network model and/or parameters or variables of the trained neural network model may be stored in the training device and/or diagnostic device (or server). The trained neural network model may be used in predicting diagnosis assistance information by the diagnostic device and/or client device. Also, the parameters or variables of the trained neural network model may be updated by feedback obtained from the diagnostic device or client device.

2.3.7 Model Ensemble

According to an embodiment of the present invention, in a process of training a single diagnosis assistance neural network model, a plurality of sub-models may be simultaneously trained. The plurality of sub-models may have different layer structures.

In this case, the diagnosis assistance neural network model according to an embodiment of the present invention may be implemented by combining a plurality of sub-neural network models. In other words, training of a neural network model may be performed using an ensemble technique in which a plurality of sub-neural network models are combined.

When a diagnosis assistance neural network model is configured by forming an ensemble, since prediction may be performed by synthesizing results predicted from various forms of sub-neural network models, accuracy of result prediction may be further improved.

Figure 14:
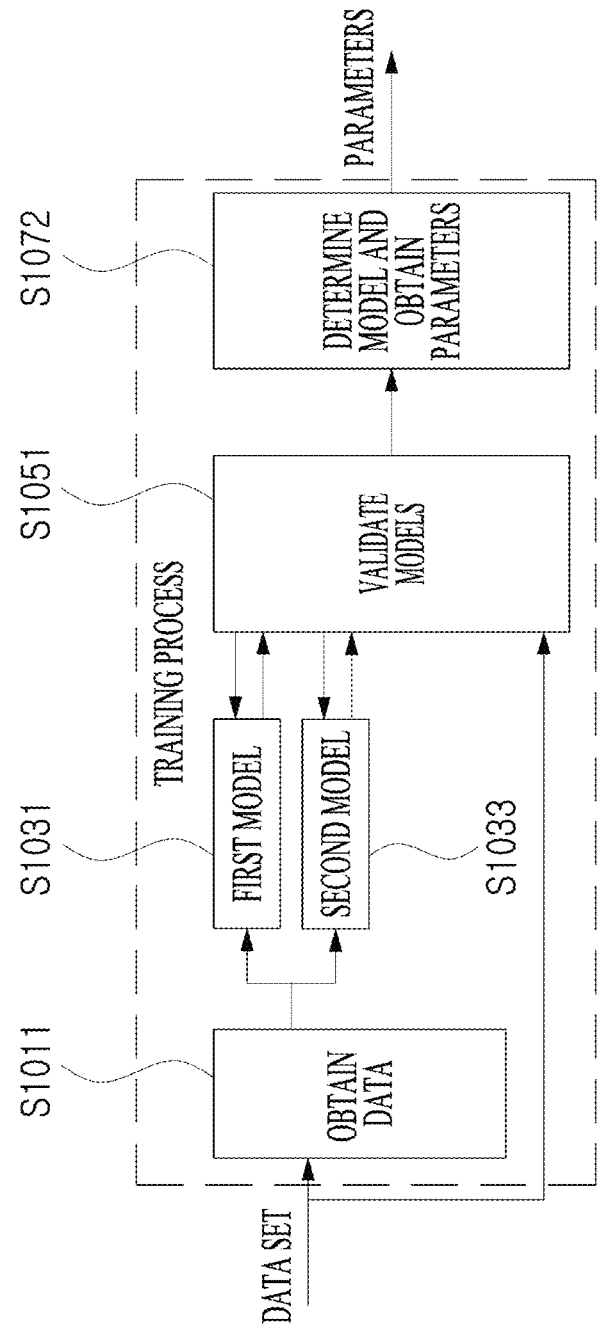
FIG. 14 is a block diagram for describing a training process of a neural network model according to an embodiment of the present invention.

FIG. 14 is a block diagram for describing a training process of a neural network model according to an embodiment of the present invention. Referring to FIG. 14, the training process of a neural network model according to an embodiment of the present invention may include obtaining a data set (S1011), training a first model (that is, first neural network model) and a second model (that is, second neural network model) using the obtained data (S1031, S1033), validating the trained first neural network model and second neural network model (S1051), and determining a final neural network model and obtaining parameters or variables thereof (S1072).

Hereinafter, some embodiments of the training process of a neural network model will be described with reference to FIG. 14.

According to an embodiment of the present invention, a plurality of sub-neural network models may obtain the same training data set and individually generate output values. In this case, an ensemble of the plurality of sub-neural network models may be determined as a final neural network model, and parameter values related to each of the plurality of sub-neural network models may be obtained as training results. An output value of the final neural network model may be set to an average value of the output values by the sub-neural network models. Alternatively, in consideration of accuracy obtained as a result of validating each of the sub-neural network models, the output value of the final neural network model may be set to a weighted average value of the output values of the sub-neural network models.

As a more specific example, when a neural network model includes a first sub-neural network model and a second sub-neural network model, optimized parameter values of the first sub-neural network model and optimized parameter values of the second sub-neural network model may be obtained by machine learning. In this case, an average value of output values (for example, probability values related to specific diagnosis assistance information) obtained from the first sub-neural network model and second sub-neural network model may be determined as an output value of the final neural network model.

According to another embodiment of the present invention, accuracy of individual sub-neural network models may be evaluated on the basis of output values by each of the plurality of sub-neural network models. In this case, any one of the plurality of sub-neural network models may be selected on the basis of the accuracy and determined as the final neural network model. A structure of the determined sub-neural network model and parameter values of the determined sub-neural network model obtained as a result of training may be stored.

As a more specific example, when a neural network model includes a first sub-neural network model and a second sub-neural network model, accuracies of the first sub-neural network model and second sub-neural network model may be obtained, and a more accurate sub-neural network model may be determined as the final neural network model.

According to still another embodiment of the present invention, one or more sub-neural network models among a plurality of neural network models may be combined, ensembles of the one or more combined sub-neural network models may be formed, and each ensemble may be evaluated, wherein a combination of sub-neural network models which forms the most accurate ensemble among the plurality of ensembles may be determined as a final neural network model. In this case, an ensemble may be formed for all possible cases of selecting one or more of the plurality of sub-neural network models, and a combination of sub-neural network models which is evaluated to be the most accurate may be determined as a final neural network model.

As a more specific example, when a neural network model includes a first sub-neural network model and a second sub-neural network model, accuracy of the first sub-neural network model, accuracy of the second sub-neural network model, and accuracy of an ensemble of the first and second sub-neural network models may be compared, and a sub-neural network model combination of the most accurate case may be determined as a final neural network model.

2.4 Embodiment 1—Control Method of Training Device

Figure 15:
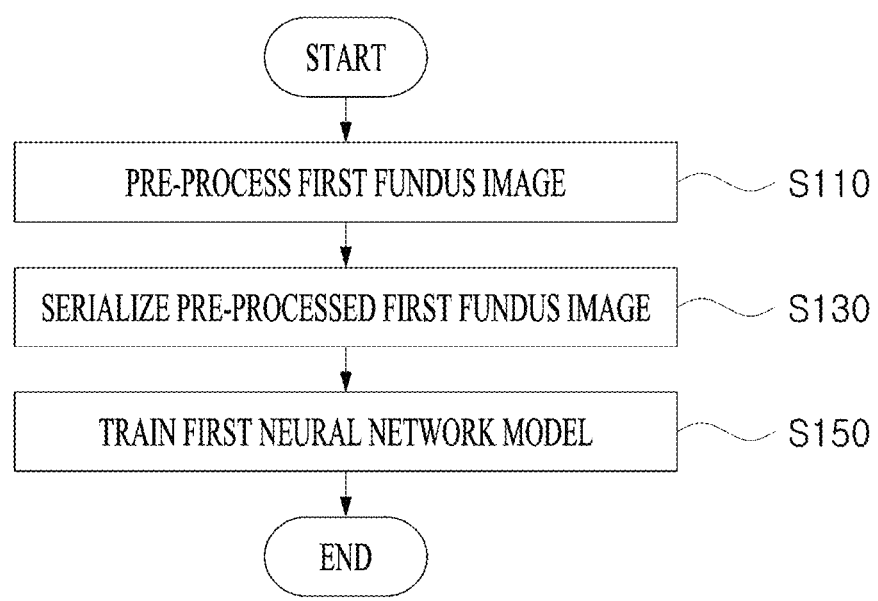
FIG. 15 is a view for describing a control method of a training device according to an embodiment of the present invention.

FIG. 15 is a view for describing a control method of a training device according to an embodiment of the present invention.

Referring to FIG. 15, the control method of a training device according to an embodiment of the present invention may include pre-processing a first fundus image (S110), serializing the pre-processed first fundus image (S130), and training a first neural network model (S150).

The control method of a training device according to an embodiment of the present invention may be a control method of a training device included in a system including a training device configured to obtain a first training data set including a plurality of fundus images, process the fundus images included in the first training data set, and train a first neural network model using the first training data set and a diagnostic device configured to obtain a target fundus image for obtaining diagnosis assistance information and obtain the diagnosis assistance information on the basis of the target fundus image by using the trained first neural network model.

The pre-processing of the first fundus image (S110) may further include pre-processing the first fundus image so that the first fundus image included in the first training data set is converted to a format suitable for training the first neural network model.

The control method of the training device according to an embodiment of the present invention may include the serializing of the pre-processed first fundus image (S130). The first fundus image may be serialized to a format that facilitates training of the neural network model.

In this case, the training of the first neural network model (S150) may further include training the first neural network model that classifies the target fundus image as a first label or a second label by using the serialized first fundus image.

The training device may obtain a second training data set which includes the plurality of fundus images and at least partially differs from the first training data set and may train a second neural network model using the second training data set.

According to an embodiment of the present invention, the control method of the training device may further include pre-processing a second fundus image so that the second fundus image included in the second data training set is suitable for training the second neural network model, serializing the pre-processed second fundus image, and training the second neural network model that classifies the target fundus image as a third label or a fourth label by using the serialized second fundus image.

Figure 16:
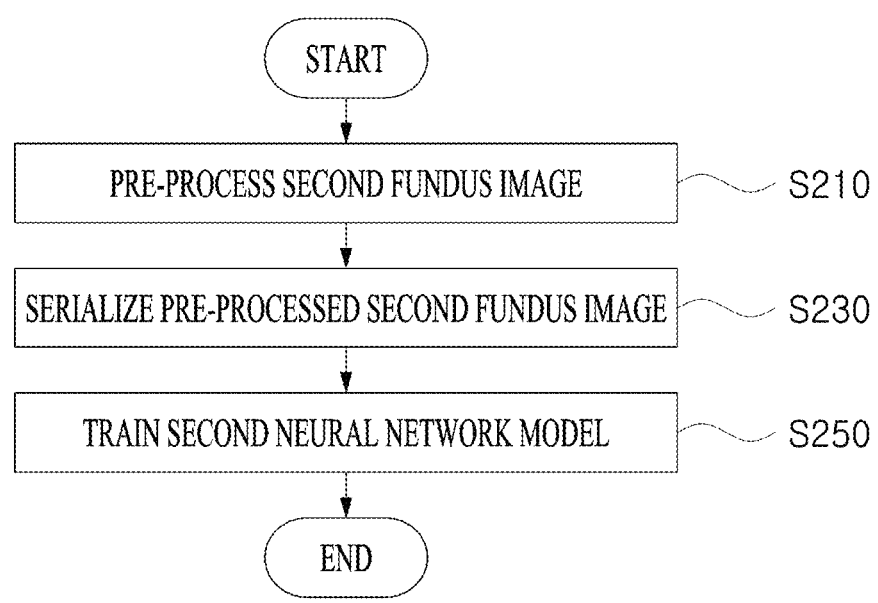
FIG. 16 is a view for describing a control method of a training device according to an embodiment of the present invention.

FIG. 16 is a view for describing a control method of a training device according to an embodiment of the present invention. Referring to FIG. 16, the control method of a training device according to an embodiment of the present invention may include pre-processing a second fundus image (S210), serializing the pre-processed second fundus image (S230), and training a second neural network model (S250).

Although, for convenience of description, it has been depicted in FIG. 16 that the pre-processing of the second fundus image, the serializing of the second fundus image, and the training using the second fundus image may be performed subsequent to the pre-processing of the first fundus image, the serializing of the first fundus image, and the training using the first fundus image, content of the invention is not limited thereto.

The pre-processing of the second fundus image included in the second training data set, the serializing of the second fundus image, and the training using the second fundus image may be performed independently of the above-described pre-processing of the first fundus image, serializing of the first fundus image, and training using the first fundus image. The pre-processing of the second fundus image included in the second training data set, the serializing of the second fundus image, and the training using the second fundus image may be performed in parallel with the above-described pre-processing of the first fundus image, serializing of the first fundus image, and training using the first fundus image. In other words, the pre-processing of the second fundus image included in the second training data set, the serializing of the second fundus image, and the training using the second fundus image are not necessarily performed subsequent or prior to the above-described pre-processing of the first fundus image, serializing of the first fundus image, and training using the first fundus image. The process related to the first fundus image and the process related to the second fundus image may be performed without dependence on each other.

First pre-processing performed in relation to the fundus image included in the first training data set may be distinguished from second pre-processing performed in relation to the fundus image included in the second training data set. For example, the first pre-processing may be pre-processing for emphasizing a blood vessel, and the second pre-processing may be pre-processing for modulating color. Each pre-processing may be determined in consideration of diagnosis assistance information desired to be obtained through each neural network model.

The control method of the training device according to an embodiment of the present invention may further include validating the first neural network model by evaluating accuracy of the trained first neural network model by using a first validation data set that is at least partially distinguished from the first training data set and validating the second neural network model by evaluating accuracy of the trained second neural network model by using a second validation data set that is at least partially distinguished from the second training data set. In this case, validation of the first neural network model and validation of the second neural network model may be performed independently of each other.

Serialized first fundus images may be sequentially stored in a first queue, and a predetermined unit volume of the serialized fundus images stored in the first queue may be used each time in training the first neural network model. Serialized second fundus images may be sequentially stored in a second queue distinguished from the first queue, and a predetermined unit volume of the serialized fundus images stored in the second queue may be used each time in training the second neural network model.

The first neural network model may include a first sub-neural network model and a second sub-neural network model. In this case, classifying a target fundus image as the first label or the second label may be performed by simultaneously taking into consideration a first predicted value predicted by the first sub-neural network model and a second predicted value predicted by the second sub-neural network model.

The second neural network model may include a third sub-neural network model and a fourth sub-neural network model. In this case, classifying a target fundus image as the third label or the fourth label may be performed by simultaneously taking into consideration a third predicted value predicted by the third sub-neural network model and a fourth predicted value predicted by the fourth sub-neural network model.

The first training data set may include at least some of fundus images labeled with the first label, and the second training data set may include at least some of fundus images labeled with the third label. In this case, the fundus images labeled with the first label may be the same as at least some of the fundus images labeled with the third label.

The first label may be a normal label indicating that a patient corresponding to the target fundus image is normal in relation to a first finding, and the second label may be an abnormal label indicating that the patient is abnormal in relation to a second finding.

The pre-processing of the first fundus image may include cropping the first fundus image so that a reference aspect ratio is satisfied and changing the size of the first fundus image.

The pre-processing of the first fundus image may further include, by a processing unit, applying a blood vessel emphasizing filter to the fundus image so that a blood vessel included in the first fundus image is emphasized.

Serialized first fundus images may be sequentially stored in a queue, and a predetermined number of the serialized first fundus images stored in the queue may be used each time in training the first neural network model. When the capacity of the serialized first fundus images which have not been used in the training of the first neural network model is reduced to a reference amount or lower, the queue may request for supplementation of the serialized first fundus images.

The first finding may be any one of a finding of retinal hemorrhage, a finding of generation of retinal exudates, a finding of opacity of crystalline lens, and a finding of diabetic retinopathy.

Figure 17:
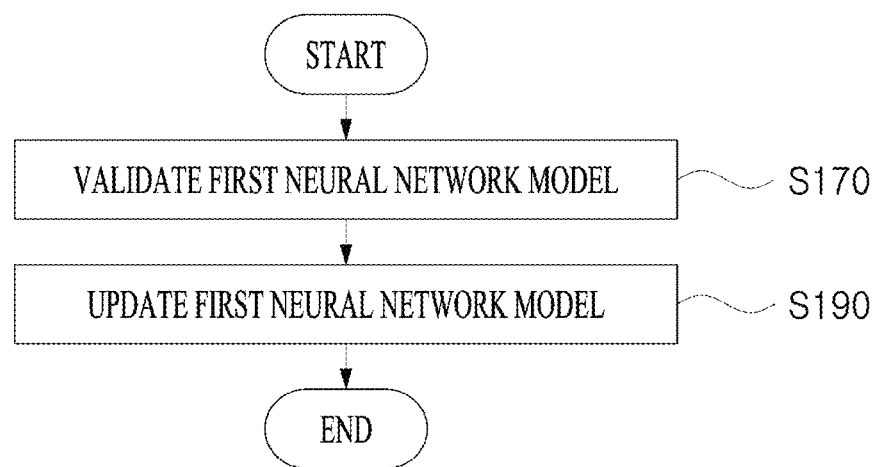
FIG. 17 is a view for describing a control method of a training device according to an embodiment of the present invention.

FIG. 17 is a view for describing a control method of a training device according to an embodiment of the present invention.

Referring to FIG. 17, the control method of the training device according to an embodiment of the present invention may further include validating the first neural network model (S170) and updating the first neural network model (S190).

The validating of the first neural network model (S170) may further include validating the first neural network model by evaluating accuracy of the trained first neural network model by using the first validation data set that is at least partially distinguished from the first training data set.

The updating of the first neural network model (S190) may further include updating the first neural network model by reflecting a validation result obtained from the validating of the first neural network model (S170).

Meanwhile, the first neural network model may include a first sub-neural network model and a second sub-neural network model. In this case, the training of the first neural network model may include validating the first sub-neural network model using the first validation data set to obtain accuracy of the first sub-neural network model, validating the second sub-neural network model using the first validation data set to obtain accuracy of the second sub-neural network model, and comparing the accuracy of the first sub-neural network model and the accuracy of the second sub-neural network model to determine a more accurate sub-neural network model as the final neural network model.

3. Diagnosis Assistance Process

According to an embodiment of the present invention, a diagnosis assistance process (or diagnostic process) in which diagnosis assistance information is obtained using a neural network model may be provided. As a specific example, by the diagnosis assistance process, diagnosis assistance information (for example, diagnostic information or findings information) may be predicted through a diagnosis assistance neural network model trained using a fundus image.

The diagnosis assistance process which will be described below may be performed by a diagnostic device.

3.1 Diagnostic Unit

According to an embodiment of the present invention, a diagnostic process may be performed by a diagnostic unit 200. The diagnostic unit 200 may be provided in the above-described diagnostic device.

Figure 18:
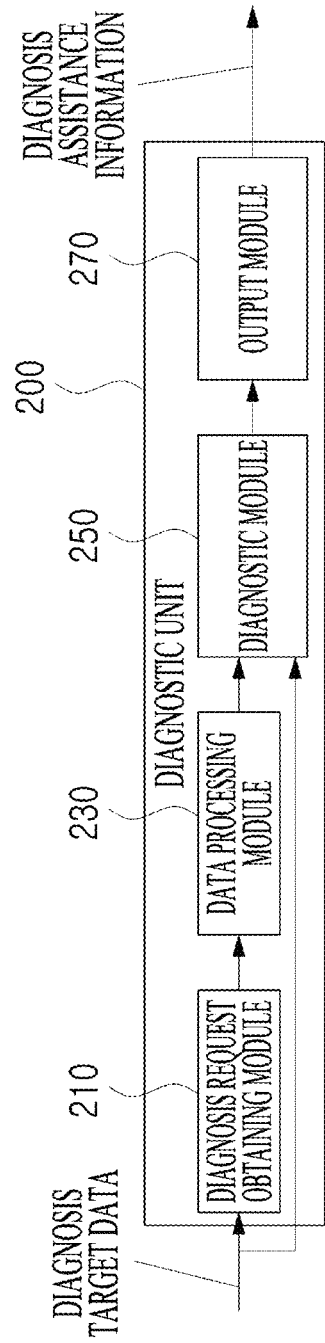
FIG. 18 is a view for describing a configuration of a diagnostic unit according to an embodiment of the present invention.

FIG. 18 is a view for describing a configuration of the diagnostic unit 200 according to an embodiment of the present invention. Referring to FIG. 18, the diagnostic unit 200 may include a diagnosis request obtaining module 210, a data processing module 230, a diagnostic module 250, and an output module 270.

As will be described below, the modules may perform individual steps of a data processing process and a training process. However, not all of the elements described with reference to FIG. 18 and functions performed by the elements are essential, and some elements may be added or omitted according to an aspect of diagnosis.

3.2 Obtaining Data and Diagnosis Request

The diagnostic device according to an embodiment of the present invention may obtain diagnosis target data and obtain diagnosis assistance information on the basis of the obtained diagnosis target data. The diagnosis target data may be image data. The obtaining of the data and obtaining of a diagnosis request may be performed by the diagnosis request obtaining module of the above-described diagnostic unit.

Figure 19:
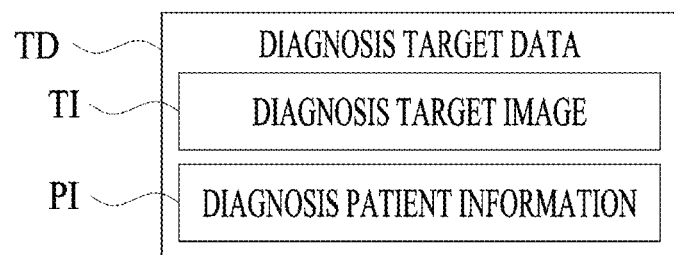
FIG. 19 is a view for describing diagnosis target data according to an embodiment of the present invention.

FIG. 19 is a view for describing diagnosis target data TD according to an embodiment of the present invention. Referring to FIG. 19, the diagnosis target data TD may include a diagnosis target image TI and diagnosis target patient information PI.

The diagnosis target image TI may be an image for obtaining diagnosis assistance information on a diagnosis target patient. For example, the diagnosis target image may be a fundus image. The diagnosis target image TI may have any one format among JPG, PNG, DCM (DICOM), BMP, GIF, and TIFF.

The diagnosis patient information PI may be information for identifying a patient to be diagnosed. Alternatively, the diagnosis patient information PI may be characteristic information of a patient or an image to be diagnosed. For example, the diagnosis patient information PI may include information such as the date and time of imaging and imaging equipment of an image to be diagnosed or information such as an identification (ID) number, an ID, name, age, or weight of a patient to be diagnosed. When the image to be diagnosed is a fundus image, the diagnosis patient information PI may further include eye-related information such as left eye/right eye information on whether the corresponding fundus image is an image of the left eye or an image of the right eye.

The diagnostic device may obtain a diagnosis request. The diagnostic device may obtain diagnosis target data together with the diagnosis request. When the diagnosis request is obtained, the diagnostic device may obtain diagnosis assistance information using a trained diagnosis assistance neural network model. The diagnostic device may obtain a diagnosis request from a client device. Alternatively, the diagnostic device may obtain a diagnosis request from a user through a separately-provided input means.

3.3 Date Processing Process

Obtained data may be processed. Data processing may be performed by the data processing module of the above-described diagnostic unit.

Generally, a data processing process may be performed similar to the data processing process in the above-described training process. Hereinafter, the data processing process in the diagnostic process will be described focusing on differences from the data processing process in the training process.

In the diagnostic process, the diagnostic device may obtain data as in the training process. In this case, the obtained data may have the same format as the data obtained in the training process. For example, when the training device has trained a diagnosis assistance neural network model using image data in the DCM format in the training process, the diagnostic device may obtain the DCM image and obtain diagnosis assistance information using the trained neural network model.

In the diagnostic process, the obtained image to be diagnosed may be resized similar to the image data used in the training process. To efficiently perform prediction of diagnosis assistance information through the trained diagnosis assistance neural network model, the form of the image to be diagnosed may be adjusted to have a suitable volume, size, and/or aspect ratio.

For example, when an image to be diagnosed is a fundus image, resizing of the image such as removing an unnecessary portion of the image or reducing the size of the image may be performed to predict diagnostic information on the basis of the fundus image.

In the diagnostic process, similar to the image data used in the training process, a pre-processing filter may be applied to the obtained image to be diagnosed. A suitable filter may be applied to the image to be diagnosed so that accuracy of prediction of diagnosis assistance information through a trained diagnosis assistance neural network model is further improved.

For example, when an image to be diagnosed is a fundus image, pre-processing that facilitates prediction of correct diagnostic information, for example, image pre-processing that causes a blood vessel to be emphasized or image pre-processing that causes a specific color to be emphasized or weakened, may be applied to the image to be diagnosed.

In the diagnostic process, similar to the image data used in the training process, the obtained image to be diagnosed may be serialized. The image to be diagnosed may be converted to a form that facilitates driving of a diagnostic model in a specific work frame or may be serialized.

The serializing of the image to be diagnosed may be omitted. This may be because, in the diagnostic process, the number of data processed at one time by a processor is not large unlike in the training process, and thus the burden on data processing speed is relatively small.

In the diagnostic process, similar to the image data used in the training process, the obtained image to be diagnosed may be stored in a queue. However, since the number of data being processed is smaller in the diagnostic process in comparison to that in the training process, storing data in a queue may also be omitted.

Meanwhile, since an increase in the number of data is not required in the diagnostic process, it is preferable that, in order to obtain accurate diagnosis assistance information, the process of data augmentation or image augmentation is not used, unlike in the training process.

3.4 Diagnostic Process

According to an embodiment of the present invention, a diagnostic process using a trained neural network model may be disclosed. The diagnostic process may be performed by the above-described diagnostic device. The diagnostic process may be performed by the above-described diagnostic server. The diagnostic process may be performed by the control unit of the above-described diagnostic device. The diagnostic process may be performed by the diagnostic module of the above-described diagnostic unit.

Figure 20:
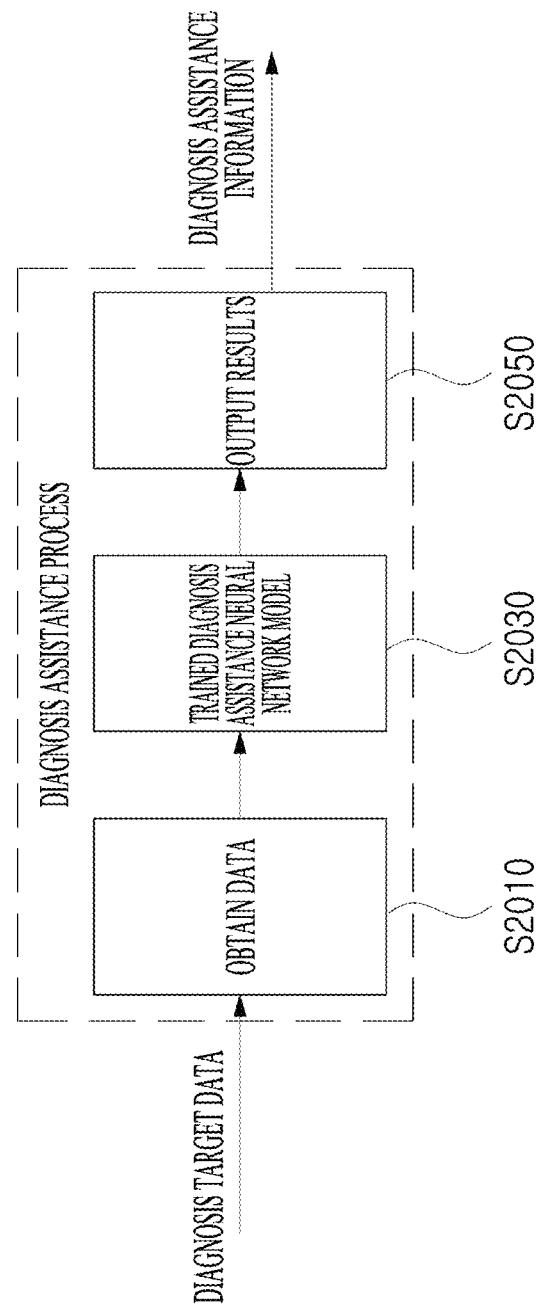
FIG. 20 is a view for describing a diagnostic process according to an embodiment of the present invention.

FIG. 20 is a view for describing a diagnostic process according to an embodiment of the present invention. Referring to FIG. 20, the diagnostic process may include obtaining diagnosis target data (S2010), using a trained neural network model (S2030), and obtaining and outputting a result corresponding to the obtained diagnosis target data (S2050). However, data processing may be selectively performed.

Hereinafter, each step of the diagnostic process will be described with reference to FIG. 20.

3.4.1 Data Input

According to an embodiment of the present invention, the diagnostic module may obtain diagnosis target data. The obtained data may be data processed as described above. For example, the obtained data may be a patient's fundus image data to which pre-processing that causes the size to be adjusted and a blood vessel to be emphasized is applied. According to an embodiment of the present invention, a left eye image and a right eye image of a single patient may be input together as diagnosis target data.

3.4.2 Data Classification

A diagnosis assistance neural network model provided in the form of a classifier may classify input diagnosis target images into a positive class or a negative class in relation to a predetermined label.

A trained diagnosis assistance neural network model may receive diagnosis target data and output a predicted label.

The trained diagnosis assistance neural network model may output a predicted value of diagnosis assistance information. Diagnosis assistance information may be obtained using the trained diagnosis assistance neural network model. The diagnosis assistance information may be determined on the basis of the predicted label.

For example, the diagnosis assistance neural network model may predict diagnostic information (that is, information on the presence of a disease) or findings information (that is, information on the presence of abnormal findings) related to an eye disease or a systemic disease of the patient. In this case, the diagnostic information or findings information may be output in the form of a probability. For example, the probability that the patient has a specific disease or the probability that there may be a specific abnormal finding in the patient's fundus image may be output. When a diagnosis assistance neural network model provided in the form of a classifier is used, a predicted label may be determined in consideration of whether an output probability value (or predicted score) exceeds a threshold value.

As a specific example, a diagnosis assistance neural network model may output a probability value with respect to the presence of diabetic retinopathy in a patient with the patient's fundus image as a diagnosis target image. When a diagnosis assistance neural network model in the form of a classifier that assumes 1 as normal is used, a patient's fundus image may be input to the diagnosis assistance neural network model, and in relation to whether the patient has diabetic retinopathy, a normal:abnormal probability value may be obtained in the form of 0.74:0.26 or the like.

Although the case in which data is classified using the diagnosis assistance neural network model in the form of a classifier has been described herein, the present invention is not limited thereto, and a specific diagnosis assistance numerical value (for example, blood pressure or the like) may also be predicted using a diagnosis assistance neural network model implemented in the form of a regression model.

According to another embodiment of the present invention, suitability information on an image may be obtained. The suitability information may indicate whether a diagnosis target image is suitable for obtaining diagnosis assistance information using a diagnosis assistance neural network model.

The suitability information of an image may be quality information. The quality information or suitability information may indicate whether a diagnosis target image reaches a reference level.

For example, when a diagnosis target image has a defect due to a defect of imaging equipment or an influence of an illumination during imaging, a result indicating that the diagnosis target image is unsuitable may be output as suitability information of the corresponding diagnosis target image. When a diagnosis target image includes noise at a predetermined level or higher, the diagnosis target image may be determined as being unsuitable.

The suitability information may be a value predicted using a neural network model. Alternatively, the suitability information may be information obtained through a separate image analysis process.

According to an embodiment, even when an image is classified as unsuitable, diagnosis assistance information may be obtained on the basis of the unsuitable image.

According to an embodiment, an image classified as unsuitable may be reexamined by a diagnosis assistance neural network model.

In this case, the diagnosis assistance neural network model that performs the reexamination may differ from a diagnosis assistance neural network model that performs initial examination. For example, the diagnostic device may store a first diagnosis assistance neural network model and a second diagnosis assistance neural network model, and an image classified as unsuitable through the first diagnosis assistance neural network model may be examined through the second diagnosis assistance neural network model.

According to still another embodiment of the present invention, a class activation map (CAM) may be obtained from a trained neural network model. Diagnosis assistance information may include a CAM. The CAM may be obtained together with other diagnosis assistance information.

The CAM may be obtained optionally. For example, the CAM may be extracted and/or output when diagnostic information or findings information obtained by a diagnosis assistance model is classified into an abnormal class.

3.5 Output of Diagnosis Assistance Information

Diagnosis assistance information may be determined on the basis of a label predicted from a diagnosis assistance neural network model.

Output of diagnosis assistance information may be performed by the output module of the above-described diagnostic unit. Diagnosis assistance information may be output from the diagnostic device to a client device. Diagnosis assistance information may be output from the diagnostic device to a server device. Diagnosis assistance information may be stored in the diagnostic device or diagnostic server. Diagnosis assistance information may be stored in a separately-provided server device or the like.

Diagnosis assistance information may be managed by being formed into a database. For example, obtained diagnosis assistance information may be stored and managed together with a diagnosis target image of a subject according to an identification number of the corresponding subject. In this case, the diagnosis target image and diagnosis assistance information of the patient may be managed in chronological order. By managing the diagnosis assistance information and diagnosis target image in time series, tracking personal diagnostic information and managing history thereof may be facilitated.

Diagnosis assistance information may be provided to a user. The diagnosis assistance information may be provided to the user through an output means of a diagnostic device or client device. The diagnosis assistance information may be output through a visual or aural output means provided in the diagnostic device or client device so that the user may recognize the diagnosis assistance information.

According to an embodiment of the present invention, an interface for effectively providing diagnosis assistance information to a user may be provided. Such a user interface will be described in more detail below in Section "5. User interface."

When a CAM is obtained by a neural network model, an image of the CAM may be provided together. The image of the CAM may be selectively provided. For example, the CAM image may not be provided when diagnostic information obtained through a diagnosis assistance neural network model is normal findings information or normal diagnostic information, and the CAM image may be provided together for more accurate clinical diagnosis when the obtained diagnostic information is abnormal findings information or abnormal diagnostic information.

When an image is classified as unsuitable, suitability information of the image may be provided together. For example, when an image is classified as unsuitable, diagnosis assistance information and "unsuitable" judgment information obtained according to the corresponding image may be provided together.

A diagnosis target image that has been judged to be unsuitable may be classified as an image to be retaken. In this case, a retake guide for a target patient of the image classified as an image to be retaken may be provided together with the suitability information.

Meanwhile, in response to providing of diagnosis assistance information obtained through a neural network model, feedback related to training of the neural network model may be obtained. For example, feedback for adjusting a parameter or hyperparameter related to training of the neural network model may be obtained. The feedback may be obtained through a user input unit provided in the diagnostic device or client device.

According to an embodiment of the present invention, diagnosis assistance information corresponding to a diagnosis target image may include level information. The level information may be selected among a plurality of levels. The level information may be determined on the basis of diagnostic information and/or findings information obtained through a neural network model. The level information may be determined in consideration of suitability information or quality information of a diagnosis target image. When a neural network model is a classifier model that performs multiclass classification, the level information may be determined in consideration of a class into which a diagnosis target image is classified by the neural network model. When a neural network model is a regression model that outputs a numerical value related to a specific disease, the level information may be determined in consideration of the output numerical value.

For example, diagnosis assistance information obtained corresponding to a diagnosis target image may include any one level information selected from a first level information and a second level information. When abnormal findings information or abnormal diagnostic information is obtained through a neural network model, the first level information may be selected as the level information. When abnormal findings information or abnormal diagnostic information is not obtained through a neural network model, the second level information may be selected as the level information. Alternatively, the first level information may be selected as the level information when a numerical value obtained through a neural network model exceeds a reference numerical value, and the second level information may be selected as the level information when the obtained numerical value is less than the reference numerical value. The first level information may indicate that strong abnormal information is present in a diagnosis target image compared with the second level information.

Meanwhile, a third level information may be selected as the level information when the quality of a diagnosis target image is determined to a reference quality or lower using image analysis or a neural network model. Alternatively, diagnosis assistance information may include the third level information together with the first or second level information.

When diagnosis assistance information includes the first level information, a first user guide may be output through an output means. The first user guide may indicate that a more precise test is required for a testee (patient) corresponding to the diagnosis assistance information. For example, the first user guide may indicate that secondary diagnosis (for example, diagnosis in a separate medical institution or a hospital transfer procedure) is required for the patient. Alternatively, the first user guide may indicate treatment required for the patient. As a specific example, when abnormal information on macular degeneration of the patient is obtained by diagnosis assistance information, the first user guide may include injection prescription and a guide on a hospital transfer procedure (for example, a list of hospitals to which transfer is possible) related to the patient.

When diagnosis assistance information includes the second level information, a second user guide may be output through an output means. The second user guide may include future care plans related to the patient corresponding to the diagnosis assistance information. For example, the second user guide may indicate the time of next visit and the next medical course.

When diagnosis target information includes the third level information, a third user guide may be output through an output means. The third user guide may indicate that a diagnosis target image has to be retaken. The third user guide may include information on the quality of the diagnosis target image. For example, the third user guide may include information on an artifact present in a diagnosis target image (for example, whether the artifact is a bright artifact or a dark artifact, or the degree thereof).

4. Diagnosis Assistance System for Multiple Labels

According to an embodiment of the present invention, a diagnosis assistance system for performing prediction on a plurality of labels (for example, a plurality of diagnosis assistance information) may be provided. For this, a diagnosis assistance neural network of the above-mentioned diagnosis assistance system may be designed to perform prediction on a plurality of labels.

Alternatively, in the above-mentioned diagnosis assistance system, a plurality of diagnosis assistance neural networks that perform prediction on different labels may be used in parallel. Hereinafter, such a parallel diagnosis assistance system will be described.

4.1 Configuration of Parallel Diagnosis Assistance System

According to an embodiment of the present invention, a parallel diagnosis assistance system for obtaining a plurality of diagnosis assistance information may be provided. The parallel diagnosis assistance system may train a plurality of neural network models for obtaining a plurality of diagnosis assistance information and obtain the plurality of diagnosis assistance information using the trained plurality of neural network models.

For example, the parallel diagnosis assistance system may train, on the basis of fundus images, a first neural network model that obtains a first diagnosis assistance information related to the presence of an eye disease of a patient and a second neural network model that obtains a second diagnosis assistance information related to the presence of a systemic disease of the patient and may output the diagnosis assistance information related to the presence of an eye disease and the presence of a systemic disease of the patient by using the trained first neural network model and the second neural network model.

Figure 21:
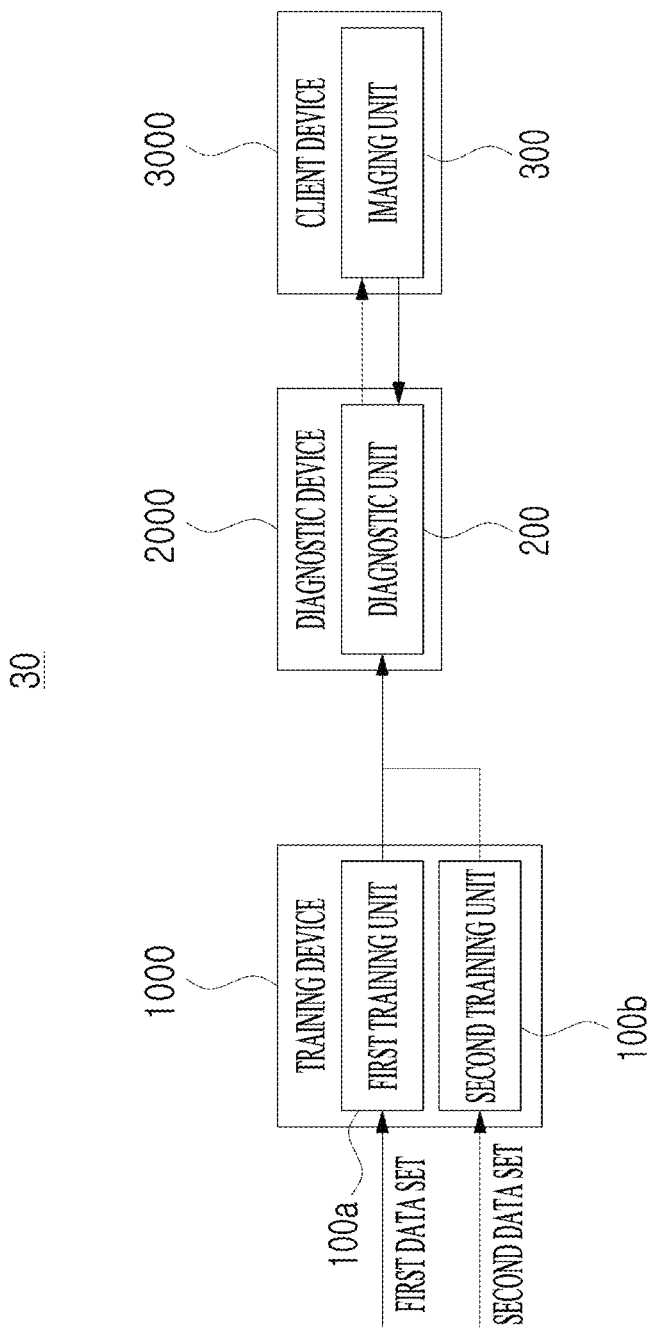
FIG. 21 is a view for describing a parallel diagnosis assistance system according to some embodiments of the present invention.
Figure 22:
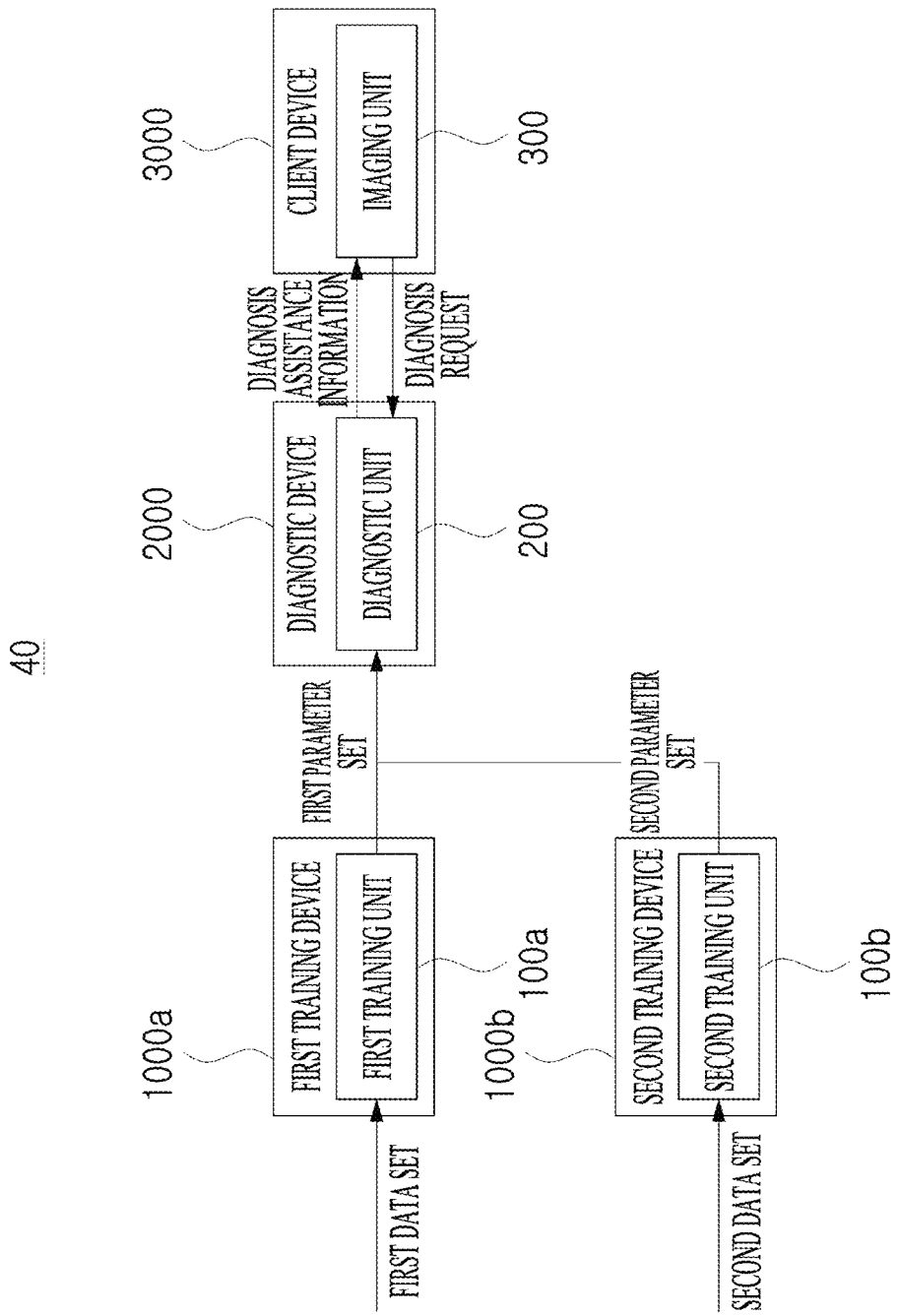
FIG. 22 is a view for describing a parallel diagnosis assistance system according to some embodiments of the present invention.

FIGS. 21 and 22 are views for describing a parallel diagnosis assistance system according to some embodiments of the present invention. Referring to FIGS. 21 and 22, the parallel diagnosis assistance system may include a plurality of training units.

Referring to FIG. 21, a parallel diagnosis assistance system 30 according to an embodiment of the present invention may include a training device 1000, a diagnostic device 2000, and a client device 3000. In this case, the training device 1000 may include a plurality of training units. For example, the training device 1000 may include a first training unit 100*a* and a second training unit 100*b*.

Referring to FIG. 22, a parallel diagnosis assistance system 40 according to an embodiment of the present invention may include a first training device 1000*a*, a second training device 1000*b*, a diagnostic device 2000, and a client device 3000. The first training device 1000*a* may include a first training unit 100*a*. The second training device 1000*b* may include a second training unit 100*b*.

Referring to FIGS. 21 and 22, the first training unit 100*a* may obtain a first data set and output a first parameter set of a first neural network model obtained as a result of training the first neural network model. The second training unit 100*b* may obtain a second data set and output a second parameter set of a second neural network model obtained as a result of training the second neural network model.

The diagnostic device 2000 may include a diagnostic unit 200. Description similar to that given above with reference to FIG. 1 may be applied to the diagnostic device 2000 and the diagnostic unit 200. The diagnostic unit 200 may obtain a first diagnosis assistance information and a second diagnosis assistance information using the trained first neural network model and second neural network model through the first training unit 100*a* and the second training unit 100*b*. The diagnostic unit 200 may store parameters of the trained first neural network model and parameters of the trained second neural network model obtained from the first training unit 100*a* and the second training unit 100*b*.

The client device 3000 may include a data obtaining unit, e.g., an imaging unit 300. However, the imaging unit 300 may be substituted with other data obtaining means used for obtaining diagnosis assistance information. The client device may transmit a diagnosis request and diagnosis target data (for example, a fundus image obtained by the imaging unit) to the diagnostic device. In response to the transmitting of the diagnosis request, the client device 3000 may obtain, from the diagnostic device, a plurality of diagnosis assistance information according to the transmitted diagnosis target data.

Meanwhile, although the case in which the diagnosis assistance system 40 includes the first training unit 100*a* and the second training unit 100*b* has been described above with reference to FIGS. 21 and 22, content of the invention is not limited thereto. According to another embodiment of the present invention, a training device may include a training unit configured to obtain three or more different diagnosis assistance information. Alternatively, a diagnosis assistance system may also include a plurality of training devices configured to obtain different diagnosis assistance information The operations of the training device, the diagnostic device, and the client device will be described in more detail below.

4.2 Parallel Training Process

According to an embodiment of the present invention, a plurality of neural network models may be trained. Training processes for training the respective neural network models may be performed in parallel.

4.2.1 Parallel Training Units

Training processes may be performed by a plurality of training units. The training processes may be performed independently of each other. The plurality of training units may be provided in a single training device or respectively provided in a plurality of training devices.

Figure 23:
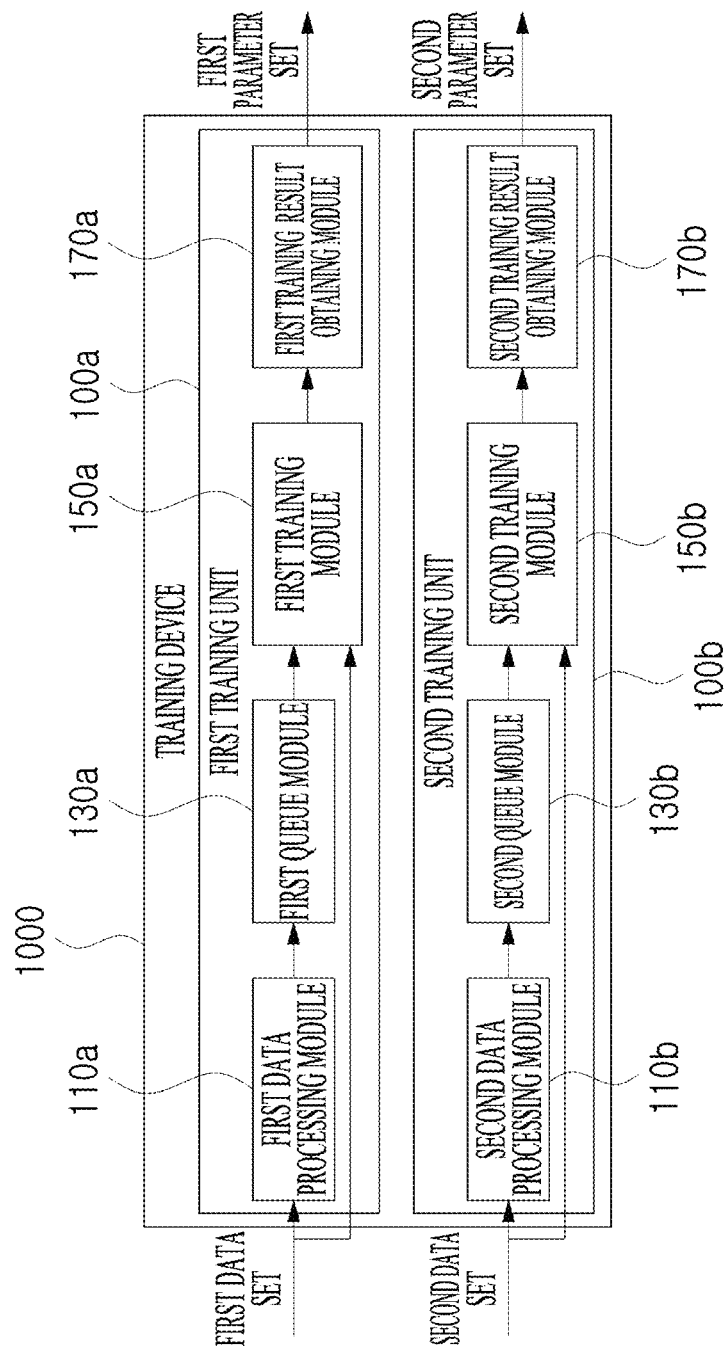
FIG. 23 is a view for describing a configuration of a training device including a plurality of training units according to an embodiment of the present invention.

FIG. 23 is a view for describing a configuration of a training device including a plurality of training units according to an embodiment of the present invention. The configuration and operation of each of the first training unit 100*a* and the second training unit 100*b* may be implemented similar to those described above with reference to FIG. 9.

Referring to FIG. 23, a process of a neural network model according to an embodiment of the present invention may be performed by a training device 1000 including a first training unit 100*a* which includes a first data processing module 110*a*, a first queue module 130*a*, a first training module 150*a*, and a first training result obtaining module 170*a* and a second training unit 100*b* which includes a second data processing module 110*b*, a second queue module 130*b*, a second training module 150*b*, and a second training result obtaining module 170*b*.

Referring to FIG. 23, a training process of a neural network model according to an embodiment of the present invention may be performed by each of the first training unit 100*a* and the second training unit 100*b*. The first training unit 100*a* and the second training unit 100*b* may independently perform training of the first neural network model and the second neural network model. Referring to FIG. 23, the first training unit 100*a* and the second training unit 100*b* may be provided in the above-described training device. Alternatively, the first training unit and the second training unit may also be provided in different training devices.

4.2.2 Obtaining Parallel Data

According to an embodiment of the present invention, a plurality of training units may obtain data. The plurality of training units may obtain different data sets. Alternatively, the plurality of training units may also obtain the same data set. According to circumstances, the plurality of training units may also obtain partially common data sets. The data sets may be fundus image data sets.

A first training unit may obtain a first data set, and a second training unit may obtain a second data set. The first data set and the second data set may be distinguished from each other. The first data set and the second data set may be partially common. The first data set and the second data set may be labeled fundus image data sets.

The first data set may include data labeled as normal in relation to a first feature and data labeled as abnormal in relation to the first feature. For example, the first data set may include a fundus image labeled as normal and a fundus image labeled as abnormal in relation to the opacity of crystalline lens.

The second data set may include data labeled as normal in relation to a second feature (distinguished from the first feature) and data labeled as abnormal in relation to the second feature. For example, the second data set may include a fundus image labeled as normal and a fundus image labeled as abnormal in relation to diabetic retinopathy.

The data labeled as normal in relation to the first feature and data labeled as normal in relation to the second feature respectively included in the first data set and the second data set may be common. For example, the first data set may include a fundus image labeled as normal and a fundus image labeled as abnormal in relation to the opacity of crystalline lens, and the second data set may include a fundus image labeled as normal and a fundus image labeled as abnormal in relation to diabetic retinopathy, wherein the fundus image labeled as normal in relation to the opacity of crystalline lens included in the first data set and the fundus image labeled as normal in relation to diabetic retinopathy included in the second data set may be common.

Alternatively, the data labeled as abnormal in relation to the first feature and the data labeled as abnormal in relation to the second feature respectively included in the first data set and the second data set may also be common. That is, data labeled in relation to a plurality of features may be used in training a neural network model in relation to the plurality of features.

Meanwhile, the first data set may be a fundus image data set captured using a first method, and the second data set may be a fundus image data set captured using a second method. The first method and the second method may be any one method selected from red-free imaging, panoramic imaging, autofluorescence imaging, infrared imaging, and the like.

A data set used in each training unit may be determined in consideration of diagnosis assistance information obtained by a trained neural network model. For example, when the first training unit trains a first neural network model which desires to obtain diagnosis assistance information related to abnormal findings of the retina (for example, microaneurysms, exudates, and the like), the first training unit may obtain a first fundus image data set captured by red-free imaging. Alternatively, when the second training unit trains a second neural network model which desires to obtain diagnosis assistance information related to macular degeneration, the second training unit may obtain a second fundus image data set captured by autofluorescence imaging.

4.2.3 Parallel Data Processing

The plurality of training units may process obtained data. As described above in Section "2.2 Data processing process," each training unit may process data by applying one or more of image resizing, a pre-processing filter, image augmentation, and image serialization to obtained data. The first data processing module of the first training unit may process a first data set, and the second data processing module of the second training unit may process a second data set.

The first training unit and second training unit included in the plurality of training units may differently process obtained data sets in consideration of diagnosis assistance information obtained from neural network models respectively trained by the first training unit and the second training unit. For example, to train a first neural network model for obtaining a first diagnosis assistance information related to hypertension, the first training unit may perform pre-processing that causes blood vessels to be emphasized in fundus images included in the first fundus image data set. Alternatively, to train a second neural network model for obtaining a second diagnosis assistance information related to abnormal findings on exudates, microaneurysms, and the like of the retina, the second training unit may perform pre-processing that causes fundus images included in the second fundus image data set to be converted to red-free images.

4.2.4 Parallel Queue

The plurality of training units may store data in a queue. As described above in Section "2.2.6 Queue," each training unit may store processed data in a queue and transmit the processed data to the training module. For example, the first training unit may store a first data set in a first queue module and provide the first data set to a first training module sequentially or randomly. The second training module may store a second data set in a second queue module and provide the second data set to a second training module sequentially or randomly.

4.2.5 Parallel Training Process

The plurality of training units may train a neural network model. The training modules may independently train diagnosis assistance neural network models that perform prediction on different labels using training data sets. A first training module of the first training unit may train the first neural network model, and a second training module of the second training unit may train the second neural network model.

The plurality of diagnosis assistance neural network models may be trained in parallel and/or independently. By training models to perform prediction on different labels through the plurality of neural network models in this way, accuracy of prediction on each label may be improved, and efficiency of the prediction operation may be enhanced.

Each diagnosis assistance neural network model may be provided similar to that described above in Section "2.3.2 Model design." Each sub-training process may be performed similar to that described above in Sections 2.3.1 to 2.3.5.

A parallel training process according to an embodiment of the present invention may include training diagnosis assistance neural network models that predict different labels. The first training unit may train a first diagnosis assistance neural network model that predicts a first label. The second training unit may train a second diagnosis assistance neural network model that predicts a second label.

The first training unit may obtain a first data set and train the first diagnosis assistance neural network model that predicts the first label. For example, the first training unit may train the first diagnosis assistance neural network model that predicts the presence of macular degeneration of a patient from a fundus image by using a fundus image training data set labeled in relation to the presence of macular degeneration.

The second training unit may obtain a second data set and train the second diagnosis assistance neural network model that predicts the second label. For example, the second training unit may train the second diagnosis assistance neural network model that predicts the presence of diabetic retinopathy of a patient from a fundus image by using a fundus image training data set labeled in relation to the presence of diabetic retinopathy.

The training process of a neural network model will be described in more detail below with reference to FIGS. 24 and 25.

Figure 24:
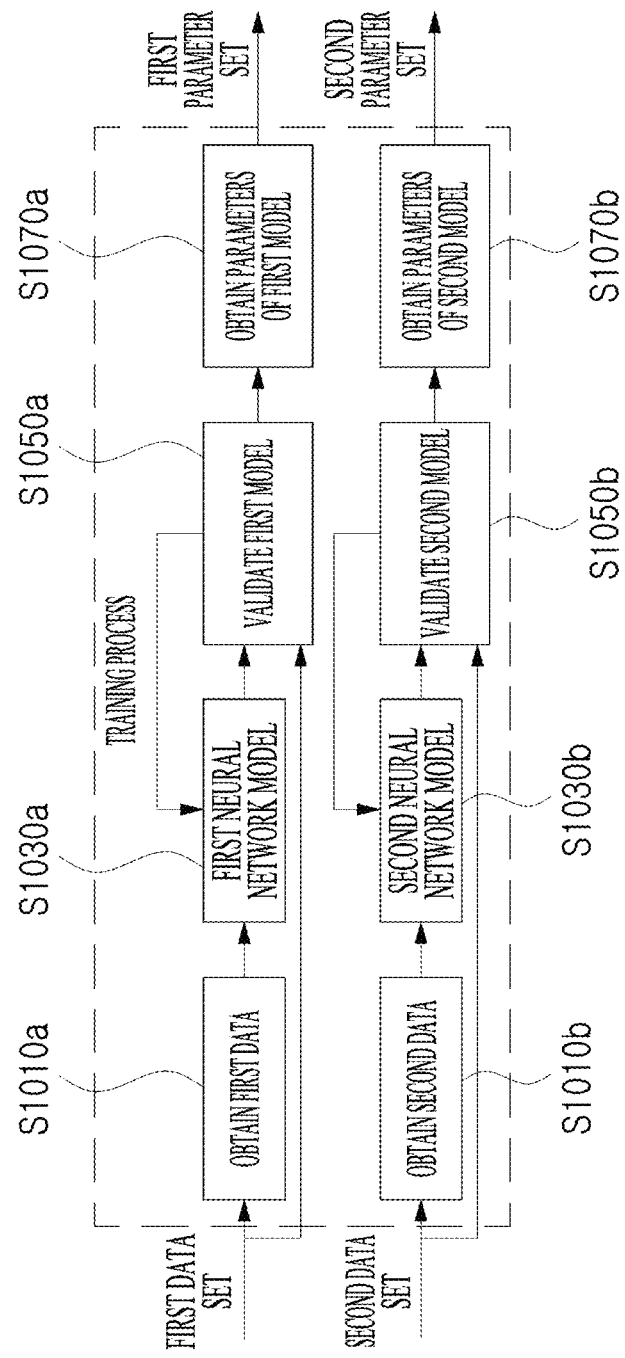
FIG. 24 is a view for describing a parallel training process according to an embodiment of the present invention.

FIG. 24 is a view for describing a parallel training process according to an embodiment of the present invention. The parallel training process may be applied to all of the cases in which the parallel diagnosis assistance system is implemented as shown in FIG. 21, implemented as shown in FIG. 22, and implemented in other forms. However, for convenience of description, description will be given below on the basis of the parallel diagnosis assistance system implemented as shown in FIG. 21.

Referring to FIG. 24, the parallel training process may include a plurality of sub-training processes that respectively train a plurality of diagnosis assistance neural network models that predict different labels. The parallel training process may include a first sub-training process that trains a first neural network model and a second sub-training process that trains a second neural network model.

For example, the first sub-training process may be performed by obtaining a first data (S1010a), using a first neural network model (S1030a), validating the first model (that is, first diagnosis assistance neural network model) (S1050a), and obtaining parameters of the first neural network model (S1070a). The second sub-training process may be performed by obtaining a second data (S1010b), using a second neural network model (1030b), validating the second neural network model (that is, second diagnosis assistance neural network model) (S1050b), and obtaining parameters of the second neural network model (S1070b).

A sub-training process may include training a neural network model by inputting training data into a sub-neural network model, comparing a label value obtained by output with the input training data to validate the model, and reflecting a validation result back to the sub-neural network model.

Each sub-training process may include obtaining result values using a neural network model to which arbitrary weight values are assigned, comparing the obtained result values with label values of training data, and performing backpropagation according to errors therebetween to optimize the weight values.

In each sub-training process, a diagnosis assistance neural network model may be validated through a validation data set distinguished from a training data set. Validation data sets for validating a first neural network model and a second neural network model may be distinguished.

The plurality of training units may obtain training results. Each training result obtaining module may obtain information on neural network models trained from the training modules. Each training result obtaining module may obtain parameter values of neural network models trained from the training units. A first training result obtaining module of the first training unit may obtain a first parameter set of a first neural network model trained from a first training module. A second training result obtaining module of the second training unit may obtain a second parameter set of a second neural network model trained from a second training module.

By each sub-training process, optimized parameter values, that is, a parameter set, of a trained neural network model may be obtained. As training is performed using more training data sets, more suitable parameter values may be obtained.

A first parameter set of a first diagnosis assistance neural network model trained by a first sub-training process may be obtained. A second parameter set of a second diagnosis assistance neural network model trained by a second sub-training process may be obtained. As training is sufficiently performed, optimized values of weights and/or bias of the first diagnosis assistance neural network and the second diagnosis assistance neural network may be obtained.

The obtained parameter set of each neural network model may be stored in the training device and/or the diagnostic device (or server). The first parameter set of the first diagnosis assistance neural network and the second parameter set of the second diagnosis assistance neural network may be stored together or separately. A parameter set of each trained neural network model may also be updated by feedback obtained from the diagnostic device or client device.

4.2.6 Parallel Ensemble Training Process

Even when a plurality of neural network models are trained in parallel, The above-described ensemble form of model training may be used. Each sub-training process may include training a plurality of sub-neural network models. The plurality of sub-models may have different layer structures. Hereinafter, unless particularly mentioned otherwise, description similar to that given above in Section 2.3.7 may be applied.

When a plurality of diagnosis assistance neural network models are trained in parallel, some sub-training processes among the sub-training processes that train the diagnosis assistance neural network models may train a single model, and other sub-training processes may train a plurality of sub-models together.

Since models are trained using ensembles in each sub-training process, more optimized forms of neural network models may be obtained in each sub-training process, and error in prediction may be reduced.

Figure 25:
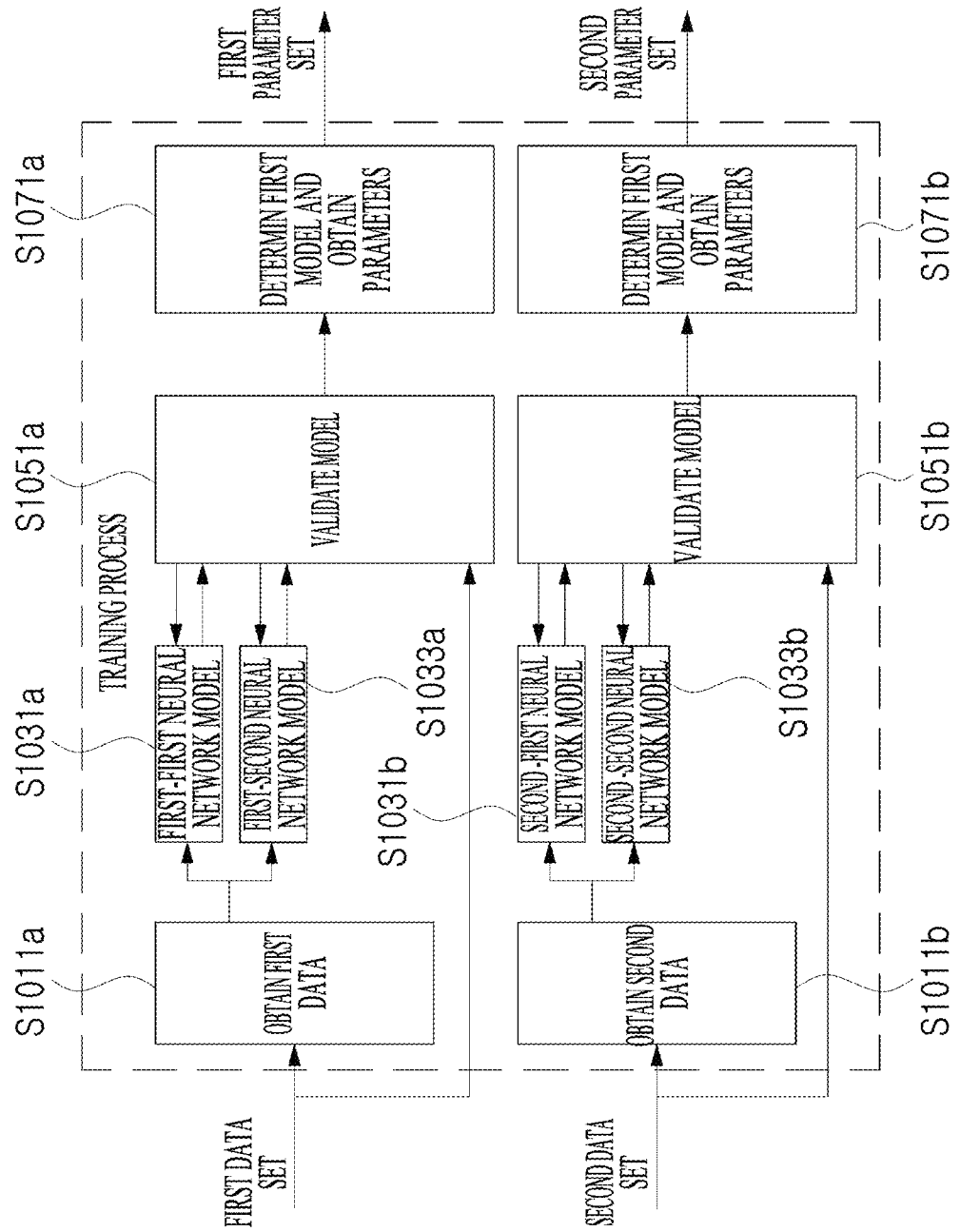
FIG. 25 is a view for describing the parallel training process according to another embodiment of the present invention.

FIG. 25 is a view for describing the parallel training process according to another embodiment of the present invention. Referring to FIG. 25, each training process may include training a plurality of sub-neural network models.

Referring to FIG. 25, a first sub-training process may be performed by obtaining a first data S1011a, using a first-first (1-1) neural network model and a first-second (1-2) neural network model (S1031a, S1033a), validating the first-first (1-1) neural network model and the first-second (1-2) neural network model (S1051a), and determining a final form of the first neural network model and parameters thereof (S1071a). A second sub-training process may be performed by obtaining a second data (S1011b), using a second-first (2-1) neural network model and a second-second (2-2) neural network model (S1031b, S1033b), validating the second-first (2-1) neural network model and the second-second (2-2) neural network model (S1051b), and determining a final form of the second model (that is, the second diagnosis assistance neural network model) and parameters thereof (S1071b).

The first neural network trained in the first sub-training process may include the first-first (1-1) neural network model and the first-second (1-2) neural network model. The first-first (1-1) neural network model and the first-second (1-2) neural network model may be provided in different layer structures. Each of the first-first (1-1) neural network model and the first-second (1-2) neural network model may obtain a first data set and output predicted labels. Alternatively, a label predicted by an ensemble of the first-first (1-1) neural network model and the first-second (1-2) neural network model may be determined as a final predicted label.

In this case, the first-first (1-1) neural network model and the first-second (1-2) neural network model may be validated using a validation data set, and a more accurate neural network model may be determined as a final neural network model. Alternatively, the first-first (1-1) neural network model, the first-second (1-2) neural network model, and the ensemble of the first-first (1-1) neural network model and the first-second (1-2) neural network model may be validated, and a neural network model form of the most accurate case may be determined as a final first neural network model.

For the second sub-training process, likewise, the most accurate form of neural network among the second-first (2-1) neural network model, the second-second (2-2) neural network model, and the ensemble of the second-first (2-1) neural network model and the second-second (2-2) neural network model may be determined as the final second model (that is, second diagnosis assistance neural network model).

Meanwhile, although, for convenience of description, the case in which each sub-training process includes two sub-models has been described above with reference to FIG. 25, this is merely an example, and the present invention is not limited thereto. A neural network model trained in each sub-training process may only include a single neural network model or include three or more sub-models.

4.3 Parallel Diagnostic Process

According to an embodiment of the present invention, a diagnostic process for obtaining a plurality of diagnosis assistance information may be provided. The diagnostic process for obtaining the plurality of diagnosis assistance information may be implemented in the form of a parallel diagnosis assistance process including a plurality of diagnostic processes which are independent from each other.

4.3.1 Parallel Diagnostic Unit

According to an embodiment of the present invention, a diagnosis assistance process may be performed by a plurality of diagnostic modules. Each diagnosis assistance process may be independently performed.

Figure 26:
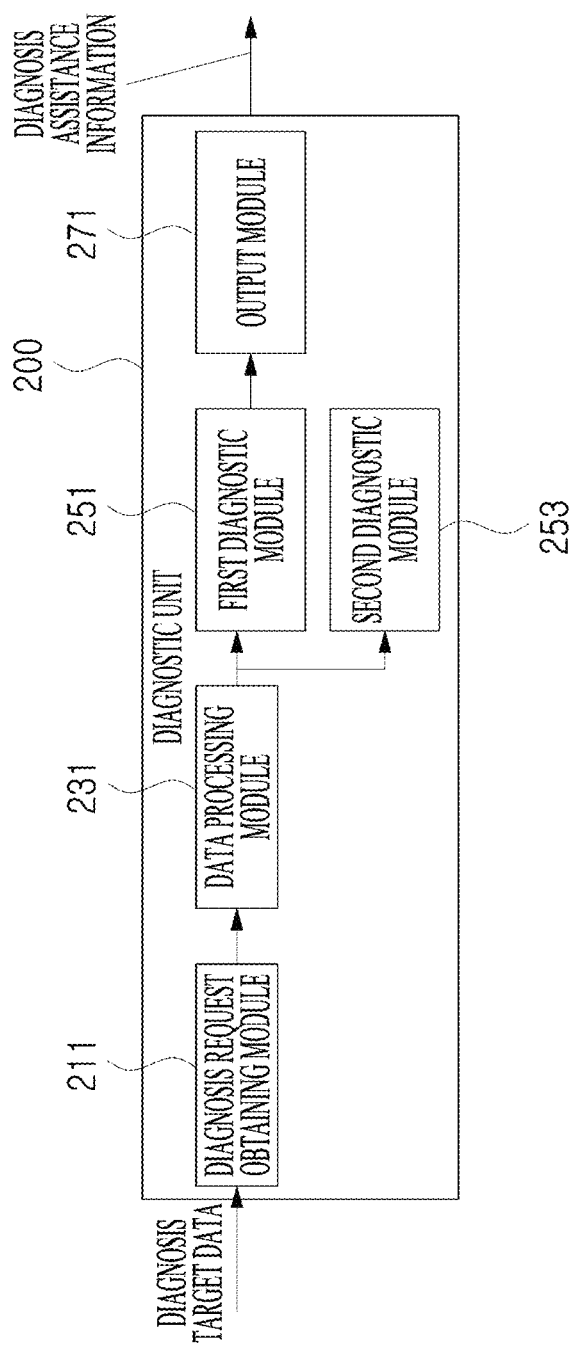
FIG. 26 is a block diagram for describing a diagnostic unit according to an embodiment of the present invention.

FIG. 26 is a block diagram for describing a diagnostic unit 200 according to an embodiment of the present invention.

Referring to FIG. 26, the diagnostic unit 200 according to an embodiment of the present invention may include a diagnosis request obtaining module 211, a data processing module 231, a first diagnostic module 251, a second diagnostic module 253, and an output module 271. Unless particularly mentioned otherwise, each module of the diagnostic unit 200 may operate similar to the diagnostic module of the diagnostic unit illustrated in FIG. 18.

In FIG. 26, the diagnosis request obtaining module 211, the data processing module 231, and the output module 271 have been illustrated as being common even when the diagnostic unit 200 includes a plurality of diagnostic modules, but the present invention is not limited to such a configuration. The diagnosis request obtaining module, the data processing module, and/or the output module may also be provided in plural. The plurality of diagnosis request obtaining modules, data processing modules, and/or output modules may also operate in parallel.

For example, the diagnostic unit 200 may include a first data processing module configured to perform first processing of an input diagnosis target image and a second data processing module configured to perform second processing of the diagnosis target image, the first diagnostic module may obtain a first diagnosis assistance information on the basis of the diagnosis target image on which the first processing has been performed, and the second diagnostic module may obtain a second diagnosis assistance information on the basis of the diagnosis target image on which the second processing has been performed. The first processing and/or second processing may be any one selected from image resizing, image color modulation, blur filter application, blood vessel emphasizing process, red-free conversion, partial region cropping, and extraction of some elements.

The plurality of diagnostic modules may obtain different diagnosis assistance information. The plurality of diagnostic modules may obtain diagnosis assistance information using different diagnosis assistance neural network models. For example, the first diagnostic module may obtain a first diagnosis assistance information related to the presence of an eye disease of a patient by using a first neural network model that predicts the presence of an eye disease of the patient, and the second diagnostic module may obtain a second diagnosis assistance information related to the presence of a systemic disease of a patient by using a second neural network model that predicts the presence of a systemic disease of the patient.

As a more specific example, the first diagnostic module may obtain a first diagnosis assistance information related to the presence of diabetic retinopathy of the patient using a first diagnosis assistance neural network model that predicts the presence of diabetic retinopathy of the patient, and the second diagnostic module may obtain a second diagnosis assistance information related to the presence of hypertension using a second diagnosis assistance neural network model that predicts the presence of hypertension of the patient.

4.3.2 Parallel Diagnostic Process

A diagnosis assistance process according to an embodiment of the present invention may include a plurality of sub-diagnostic processes. Each sub-diagnostic process may be performed using different diagnosis assistance neural network models. Each sub-diagnostic process may be performed in different diagnostic modules. For example, a first diagnostic module may perform a first sub-diagnostic process that obtains a first diagnosis assistance information through a first diagnosis assistance neural network model. Alternatively, a second diagnostic module may perform a second sub-diagnostic process that obtains a second diagnosis assistance information through a second diagnosis assistance neural network model.

The plurality of trained neural network models may output a predicted label or probability with diagnosis target data as input. Each neural network model may be provided in the form of a classifier and may classify input diagnosis target data as a predetermined label. In this case, the plurality of neural network models may be provided in forms of classifiers that are trained in relation to different characteristics. Each neural network model may classify diagnosis target data as described above in Section 3.4.2.

Meanwhile, a CAM may be obtained from each diagnosis assistance neural network model. The CAM may be obtained selectively. The CAM may be extracted when a predetermined condition is satisfied. For example, when a first diagnosis assistance information indicates that the patient is abnormal in relation to a first characteristic, a first CAM may be obtained from a first diagnosis assistance neural network model.

Figure 27:
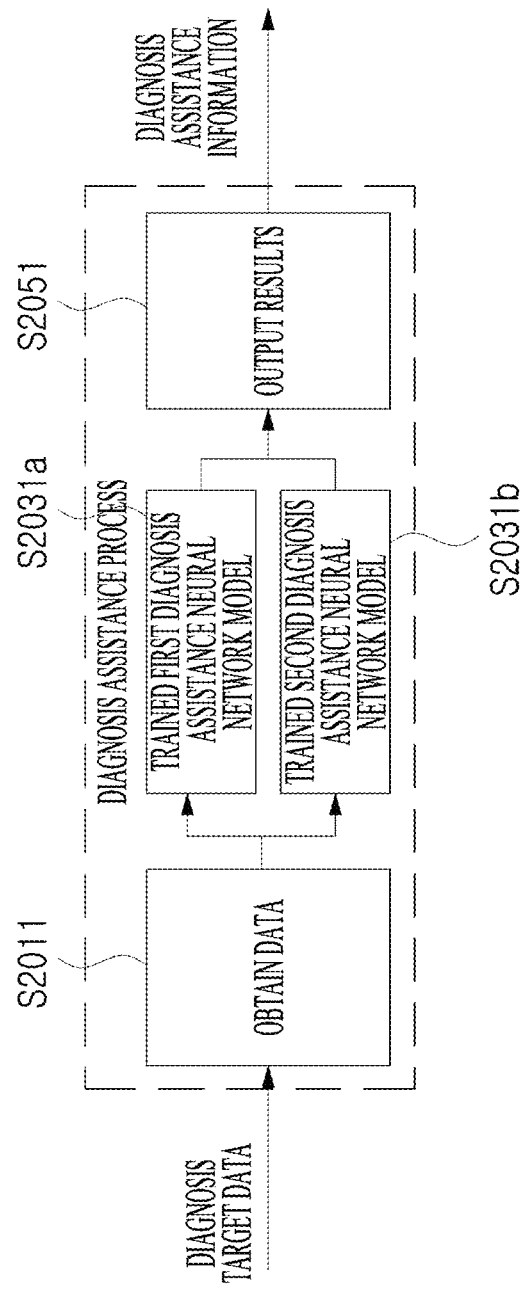
FIG. 27 is a view for describing a diagnosis assistance process according to an embodiment of the present invention.

FIG. 27 is a view for describing a diagnosis assistance process according to an embodiment of the present invention.

Referring to FIG. 27, a diagnosis assistance process according to an embodiment of the present invention may include obtaining diagnosis target data (S2011), using a first diagnosis assistance neural network model and a second diagnosis assistance neural network model (S2031a, S2031b), and obtaining diagnosis assistance information according to diagnosis target data (S2051). The diagnosis target data may be processed data.

The diagnosis assistance process according to an embodiment of the present invention may include obtaining a first diagnosis assistance information through the trained first diagnosis assistance neural network model and obtaining a second diagnosis assistance information through the trained second diagnosis assistance neural network model. The first diagnosis assistance neural network model and the second diagnosis assistance neural network model may obtain the first diagnosis assistance information and the second diagnosis assistance information respectively, on the basis of the same diagnosis target data.

For example, the first diagnosis assistance neural network model and the second diagnosis assistance neural network model may respectively obtain a first diagnosis assistance information related to the presence of macular degeneration of the patient and a second diagnosis assistance information related to the presence of diabetic retinopathy of the patient on the basis of a diagnosis target fundus image.

In addition, unless particularly described otherwise, the diagnosis assistance process described with reference to FIG. 27 may be implemented similar to the diagnosis assistance process described above with reference to FIG. 20.

4.3.3 Output of Diagnosis Assistance Information

According to an embodiment of the present invention, diagnosis assistance information may be obtained by a parallel diagnosis assistance process. The obtained diagnosis assistance information may be stored in the diagnostic device, server device, and/or client device. The obtained diagnosis assistance information may be transmitted to an external device.

A plurality of diagnosis assistance information may respectively indicate a plurality of labels predicted by a plurality of diagnosis assistance neural network models. The plurality of diagnosis assistance information may respectively correspond to the plurality of labels predicted by the plurality of diagnosis assistance neural network models. Alternatively, diagnosis assistance information may be information determined on the basis of a plurality of labels predicted by a plurality of diagnosis assistance neural network models. The diagnosis assistance information may correspond to the plurality of labels predicted by the plurality of diagnosis assistance neural network models.

In other words, a first diagnosis assistance information may be diagnosis assistance information corresponding to a first label predicted through a first diagnosis assistance neural network model. Alternatively, the first diagnosis assistance information may be diagnosis assistance information determined in consideration of a first label predicted through a first diagnosis assistance neural network model and a second label predicted through a second diagnosis assistance neural network model.

Meanwhile, CAM images obtained from a plurality of diagnosis assistance neural network models may be output. The CAM images may be output when a predetermined condition is satisfied. For example, in any one of the case in which a first diagnosis assistance information indicates that the patient is abnormal in relation to a first characteristic or the case in which a second diagnosis assistance information indicates that the patient is abnormal in relation to a second characteristic, a CAM image obtained from a diagnosis assistance neural network model, from which diagnosis assistance information indicating that the patient is abnormal has been output, may be output.

A plurality of diagnosis assistance information and/or CAM images may be provided to a user. The plurality of diagnosis assistance information or the like may be provided to the user through an output means of the diagnostic device or client device. The diagnosis assistance information may be visually output. This will be described in detail below in Section "5. User interface."

According to an embodiment of the present invention, diagnosis assistance information corresponding to a diagnosis target image may include level information. The level information may be selected from a plurality of levels. The level information may be determined on the basis of a plurality of diagnostic information and/or findings information obtained through neural network models. The level information may be determined in consideration of suitability information or quality information of a diagnosis target image. The level information may be determined in consideration of a class into which a diagnosis target image is classified by a plurality of neural network models. The level information may be determined in consideration of numerical values output from a plurality of neural network models.

For example, diagnosis assistance information obtained corresponding to a diagnosis target image may include any one level information selected from a first level information and a second level information. When at least one abnormal findings information or abnormal diagnostic information is obtained among of diagnostic information obtained through a plurality of neural network models, the first level information may be selected as the level information. When, of diagnostic information obtained through the neural network models does not include abnormal findings information or abnormal diagnostic information, the second level information may be selected as the level information.

A first level information may be selected as the level information when at least one numerical value among numerical values obtained through a neural network model exceeds a reference numerical value, and a second level information may be selected as the level information when all of the obtained numerical values are less than a reference numerical value. The first of level information may indicate that strong abnormal information is present in a diagnosis target image compared with the second of level information.

A third level information may be selected as the level information when it is determined using image analysis or a neural network model that the quality of a diagnosis target image is a reference quality or lower. Alternatively, diagnosis assistance information may include the third level information together with the first or second level information.

When diagnosis assistance information includes the first level information, a first user guide may be output through an output means. The first user guide may include matters corresponding to at least one of abnormal findings information or abnormal diagnostic information included in diagnosis assistance information. For example, the first user guide may indicate that a more precise test is required for a patient corresponding to abnormal information included in diagnosis assistance information. For example, the first user guide may indicate that secondary diagnosis (for example, diagnosis in a separate medical institution or a hospital transfer procedure) is required for the patient. Alternatively, the first user guide may indicate treatment required for the patient. As a specific example, when abnormal information on macular degeneration of the patient is obtained by diagnosis assistance information, the first user guide may include injection prescription and a guide on a hospital transfer procedure (for example, a list of hospitals to which transfer is possible) related to the patient.

When diagnosis assistance information includes the second level information, a second user guide may be output through an output means. The second user guide may include future care plans related to the patient corresponding to the diagnosis assistance information. For example, the second user guide may indicate the time of next visit and the next medical course.

When diagnosis target information includes the third level information, a third user guide may be output through an output means. The third user guide may indicate that a diagnosis target image has to be retaken. The third user guide may include information on the quality of the diagnosis target image. For example, the third user guide may include information on an artifact present in a diagnosis target image (for example, whether the artifact is a bright artifact or a dark artifact, or the degree thereof).

The first to third of level information may be output by an output unit of the client device or diagnostic device. Specifically, the first to third level information may be output through a user interface which will be described below.

4.4 Embodiment 2—Diagnosis Assistance System

A diagnosis assistance system according to an embodiment of the present invention may include a fundus image obtaining unit, a first processing unit, a second processing unit, a third processing unit, and a diagnostic information output unit.

According to an embodiment of the present invention, the diagnosis assistance system may include a diagnostic device. The diagnostic device may include a fundus image obtaining unit, a first processing unit, a second processing unit, a third processing unit, and/or a diagnostic information output unit. However, the present invention is not limited thereto, and each unit included in the diagnosis assistance system may be disposed at a proper position in a training device, a diagnostic device, a training diagnosis server, and/or a client device. Hereinafter, for convenience of description, the case in which a diagnostic device of a diagnosis assistance system includes a fundus image obtaining unit, a first processing unit, a second processing unit, a third processing unit, and a diagnostic information output unit will be described.

Figure 28:
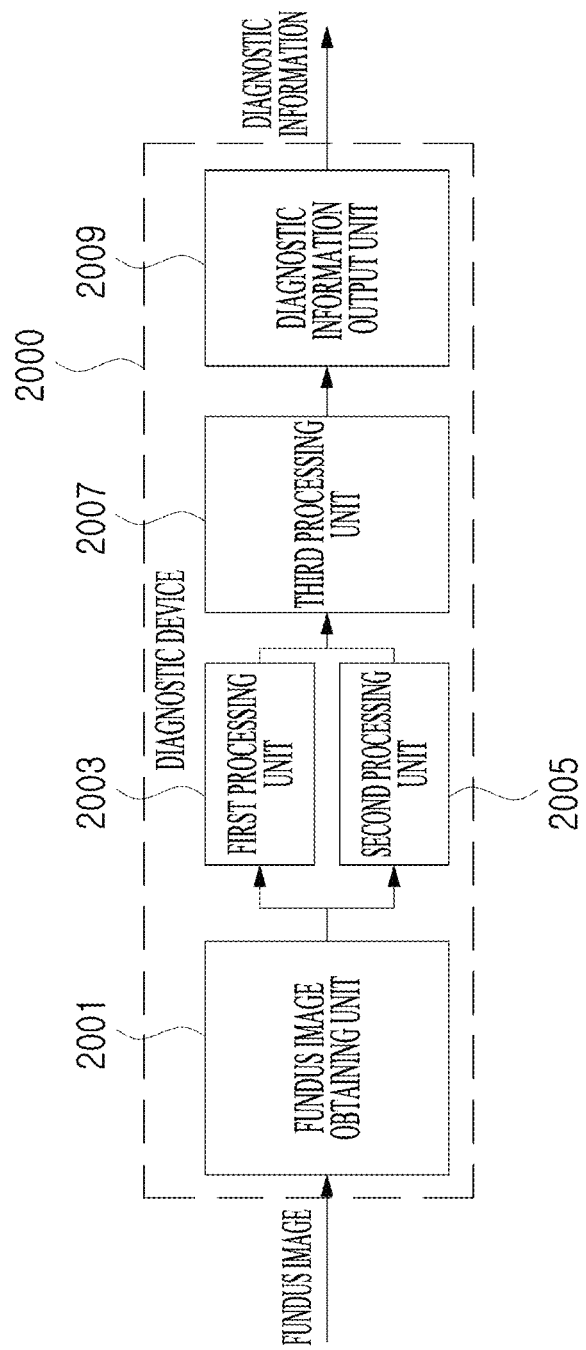
FIG. 28 is a view for describing a diagnosis assistance system according to an embodiment of the present invention.

FIG. 28 is a view for describing a diagnosis assistance system according to an embodiment of the present invention. Referring to FIG. 28, a diagnosis assistance system may include a diagnostic device, and the diagnostic device may include a fundus image obtaining unit, a first processing unit, a second processing unit, a third processing unit, and a diagnostic information output unit.

According to an embodiment of the present invention, a diagnosis assistance system that assists diagnosis of a plurality of diseases on the basis of a fundus image may include a fundus image obtaining unit configured to obtain a target fundus image which is a basis for acquiring diagnosis assistance information on a patient, a first processing unit configured to, for the target fundus image, obtain a first result related to a first finding of the patient using a first neural network model, wherein the first neural network model is trained on the basis of a first fundus image set, a second processing unit configured to, for the target fundus image, obtain a second result related to a second finding of the patient using a second neural network model, wherein the second neural network model is trained on the basis of a second fundus image set which is at least partially different from the first fundus image set, a third processing unit configured to determine, on the basis of the first result and the second result, diagnostic information on the patient, and a diagnostic information output unit configured to provide the determined diagnostic information to a user. Here, the first finding and the second finding may be used for diagnosing different diseases.

The first neural network model may be trained to classify an input fundus image as any one of a normal label and an abnormal label in relation to the first finding, and the first processing unit may obtain the first result by classifying the target fundus image as any one of the normal label and the abnormal label using the first neural network model.

The third processing unit may determine whether diagnostic information according to the target fundus image is normal information or abnormal information by taking the first result and the second result into consideration together.

The third processing unit may determine diagnostic information on the patient by assigning priority to the abnormal label so that accuracy of diagnosis is improved.

When the first label is a normal label related to the first finding, and the second label is a normal label related to the second finding, the third processing unit may determine the diagnostic information as normal. When the first label is not the normal label related to the first finding, or the second label is not the normal label related to the second finding, the third processing unit may determine the diagnostic information as abnormal.

The first finding may be related to an eye disease, and the first result may indicate whether the patient is normal in relation to the eye disease. The second finding may be related to a systemic disease, and the second result may indicate whether the patient is normal in relation to the systemic disease.

The first finding may be related to a first eye disease, and the first result may indicate whether the patient is normal in relation to the first eye disease. The second finding may be related to a second eye disease distinguished from the first eye disease, and the second result may indicate whether the patient is normal in relation to the second eye disease.

The first finding may be a finding for diagnosing a first eye disease, and the first result may indicate whether the patient is normal in relation to the first eye disease. The second finding may be a finding distinguished from the first finding for diagnosing the first eye disease, and the second result may indicate whether the patient is normal in relation to a second eye disease.

The first neural network model may include a first sub-neural network model and a second sub-neural network model, and the first result may be determined by taking a first predicted value predicted by the first sub-neural network model and a second predicted value predicted by the second sub-neural network model into consideration together.

The first processing unit may obtain a CAM related to the first label through the first neural network model, and the diagnostic information output unit may output an image of the CAM.

The diagnostic information output unit may output an image of the CAM when the diagnostic information obtained by the third processing unit is abnormal diagnostic information.

The diagnosis assistance system may further include a fourth processing unit configured to obtain quality information on the target fundus image, and the diagnostic information output unit may output the quality information on the target fundus image obtained by the fourth processing unit.

When it is determined in the fourth processing unit that the quality information on the target fundus image is at a predetermined quality level or lower, the diagnostic information output unit may provide information indicating that the quality information on the target fundus image is at the predetermined quality level or lower together with the determined diagnostic information to the user.

5. User Interface

According to an embodiment of the present invention, the above-described client device or diagnostic device may have a display unit for providing diagnosis assistance information to the user. In this case, the display unit may be provided to facilitate providing of diagnosis assistance information to the user and obtaining of feedback from the user.

As an example of the display unit, a display configured to provide visual information to the user may be provided. In this case, a graphical user interface for visually transferring diagnosis assistance information to the user may be used. For example, in a fundus diagnosis assistance system that obtains diagnosis assistance information on the basis of a fundus image, a graphical user interface for effectively displaying obtained diagnosis assistance information and helping understanding of the user may be provided.

Figure 29:
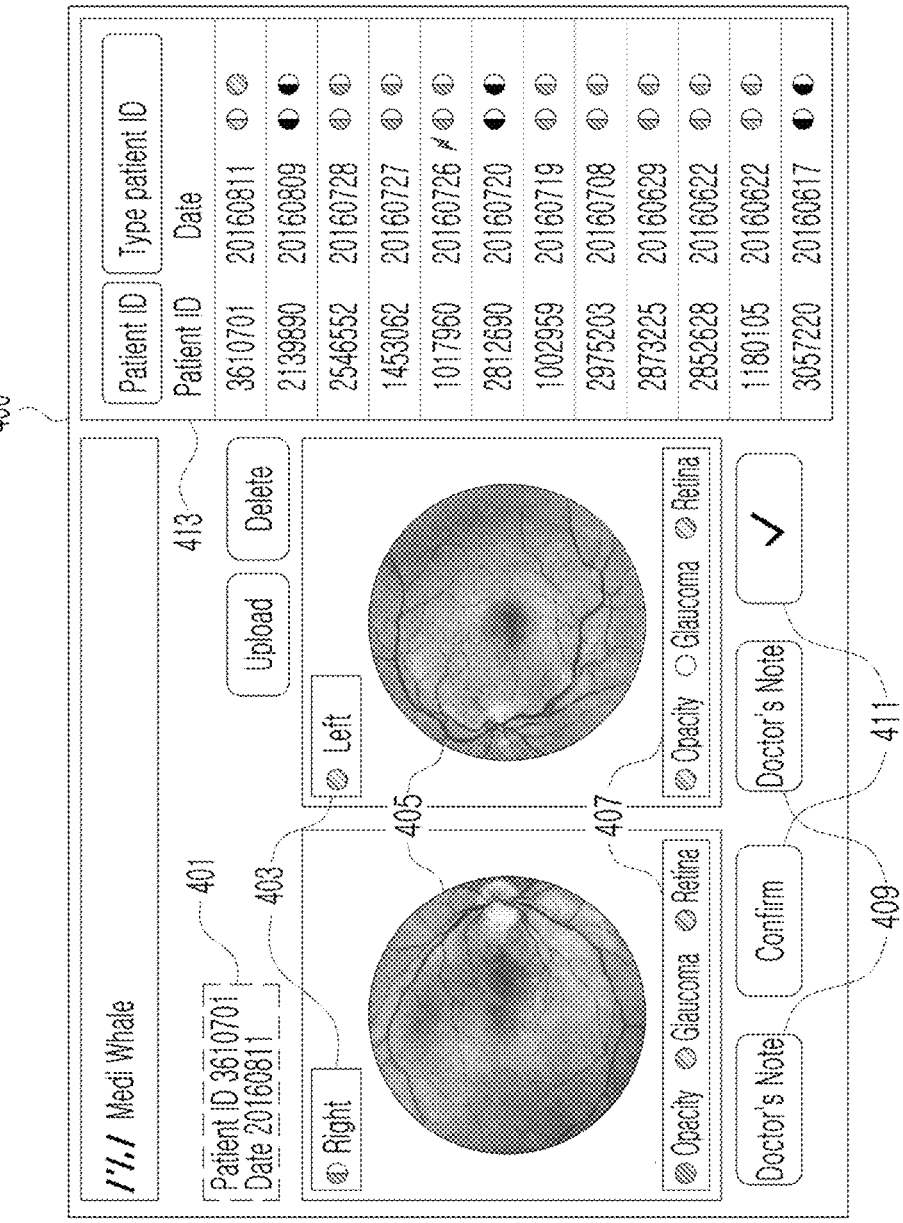
FIG. 29 is a view for describing a graphical user interface according to an embodiment of the present invention.
Figure 30:
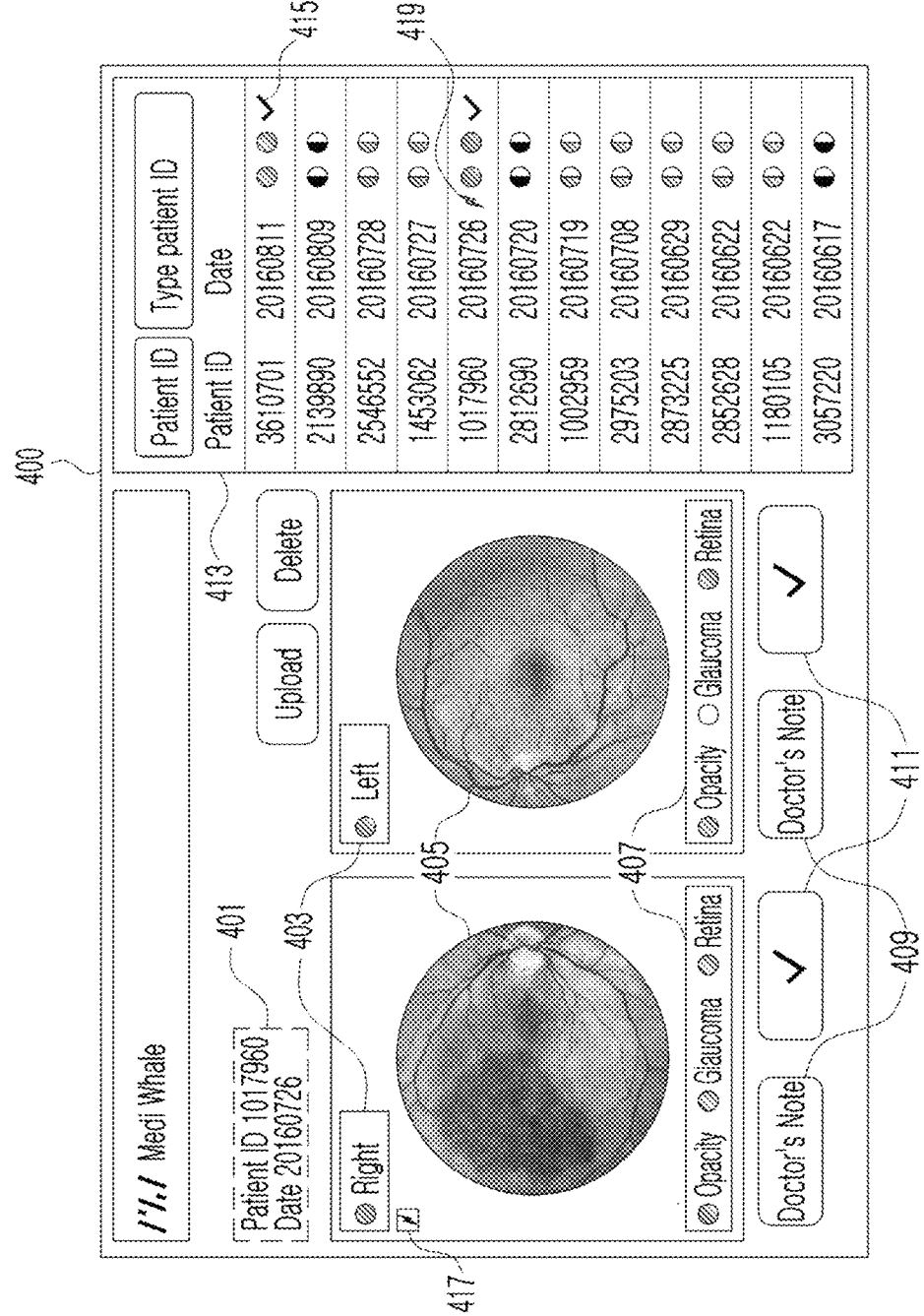
FIG. 30 is a view for describing a graphical user interface according to an embodiment of the present invention.

FIGS. 29 and 30 are views for describing a graphical user interface for providing diagnostic information to the user according to some embodiments of the present invention. Hereinafter, some embodiments of a user interface that may be used in a fundus diagnosis assistance system will be described with reference to FIGS. 29 and 30.

Referring to FIG. 29, a user interface according to an embodiment of the present invention may display identification information of a patient corresponding to a diagnosis target fundus image. The user interface may include a target image identification information display unit 401 configured to display identification information of a patient and/or imaging information (for example, the data and time of imaging) of a diagnosis target fundus image.

The user interface according to an embodiment of the present invention may include a fundus image display unit 405 configured to display a fundus image of the left eye and a fundus image of the right eye of the same patient. The fundus image display unit 405 may also display a CAM image.

The user interface according to an embodiment of the present invention may include a diagnostic information indicating unit 403 configured to indicate each of the fundus image of the left eye and the fundus image of the right eye as the image of the left eye or right eye and configured to display diagnostic information on each image and a diagnostic information indicator indicating whether the user has confirmed the diagnostic information.

Color of the diagnostic information indicator may be determined in consideration of diagnosis assistance information obtained on the basis of the target fundus image. The diagnostic information indicator may be displayed in a first color or a second color according to the diagnosis assistance information. For example, the diagnostic information indicator may be displayed in red when first to third diagnosis assistance information are obtained from a single target fundus image and when any one of the of diagnosis assistance information includes abnormal information (that is, indicates that there are abnormal findings), and the diagnostic information indicator may be displayed in green when all of the of diagnosis assistance information includes normal information (that is, indicates there are not abnormal findings).

The form of the diagnostic information indicator may be determined according to whether the user has confirmed the diagnostic information. The diagnostic information indicator may be displayed in a first form or a second form according to whether the user has confirmed the diagnostic information. For example, referring to FIG. 29, a diagnostic information indicator corresponding to a target fundus image that has been reviewed by the user may be displayed as a filled circle, and a diagnostic information indicator corresponding to a target fundus image that has not been reviewed by the user yet may be displayed as a half-circle.

The user interface according to an embodiment of the present invention may include a diagnostic information indicating unit 407 configured to indicate diagnosis assistance information. The diagnosis assistance information indicating may be disposed at each of the left eye image and the right eye image. The diagnosis assistance information indicating unit may indicate a plurality of findings information or diagnostic information.

The diagnosis assistance information indicating unit may include at least one diagnosis assistance information indicator. The diagnosis assistance information indicator may indicate corresponding diagnosis assistance information through a color change.

For example, when, in relation to a diagnosis target fundus image, a first diagnosis assistance information indicating the presence of the opacity of crystalline lens is obtained through a first diagnosis assistance neural network model, a second diagnosis assistance information indicating the presence of abnormal findings of diabetic retinopathy is obtained through a second diagnosis assistance neural network model, and a third diagnosis assistance information indicating the presence of abnormal findings of the retina is obtained through a third diagnosis assistance neural network model, the diagnostic information indicating unit may include first to third diagnosis assistance information indicators configured to respectively indicate the first diagnosis assistance information, the second diagnosis assistance information, and the third diagnosis assistance information.

As a more specific example, referring to FIG. 29, when, in relation to the left eye fundus image of the patient, a first diagnosis assistance information indicating that the obtained diagnosis assistance information is abnormal in terms of the opacity of crystalline lens is obtained, a second diagnosis assistance information indicating that the obtained diagnosis assistance information is normal (has no abnormal findings) in terms of diabetic retinopathy is obtained, and a third diagnosis assistance information indicating that the obtained diagnosis assistance information is abnormal (has abnormal findings) in terms of the retina is obtained, the diagnostic information indicating unit 407 may display a first diagnosis assistance information indicator with a first color, a second diagnosis assistance information indicator with a second color, and a third diagnosis assistance information indicator with the first color.

The user interface according to an embodiment of the present invention may obtain a user comment on a diagnosis target fundus image from the user. The user interface may include a user comment object 409 and may display a user input window in response to a user selection on the user comment object. A comment obtained from the user may also be used in updating a diagnosis assistance neural network model. For example, the user input window displayed in response to the user's selection on the user comment object may obtain a user's evaluation on diagnosis assistance information obtained through a neural network, and the obtained user's evaluation may be used in updating a neural network model.

The user interface according to an embodiment of the present invention may include a review indicating object 411 configured to display whether the user has reviewed each diagnosis target fundus image. The review indicating object may receive a user input indicating that the user's reviewing of each diagnosis target image has been completed, and display thereof may be changed from a first state to a second state. Referring to FIGS. 29 and 30, upon receiving a user input, the review indicating object may be changed from a first state in which a review request message is displayed to a second state indicating that the reviewing has been completed.

A diagnosis target fundus image list 413 may be displayed. In the list, identification information of the patient, the data on which the image has been captured, and the indicator 403 of whether the use has reviewed images of the both eyes may be displayed together.

In the diagnosis target fundus image list 413, a review completion indicator 415 indicating that the corresponding diagnosis target fundus image has been reviewed may be displayed. The review completion indicator 415 may be displayed when a user selection has been made for review indicating objects 411 of the both eyes of the corresponding images.

Referring to FIG. 30, the graphical user interface may include a poor quality warning object 417 indicating that there is an abnormality in the quality of a diagnosis target fundus image to the user when it is determined that there is an abnormality in the quality of the diagnosis target fundus image. The poor quality warning object 417 may be displayed when it is determined that the quality of the diagnosis target fundus image from the diagnostic unit is below a quality level at which appropriate diagnosis assistance information may be predicted from a diagnosis assistance neural network model (that is, a reference quality level).

In addition, referring to FIG. 30, the poor quality warning object 417 may also be displayed in the diagnosis target fundus image list 413.

According to the present invention, diagnosis assistance information can be promptly obtained on the basis of a fundus image.

Further, according to the present invention, diagnosis assistance information related to a plurality of diseases can be more accurately predicted on the basis of a fundus image.

Further, according to the present invention, obtaining an optimized neural network model for predicting diagnosis assistance information related to a plurality of diseases can be facilitated.

Advantageous effects of the present invention are not limited to those mentioned above, and other unmentioned advantageous effects should be clearly understood by one of ordinary skill in the art to which the present invention pertains from the present specification and the accompanying drawings.

While the invention has been described above with a few embodiments and the accompanying drawings, one of ordinary skill in the art may make various modifications and changes to the description above. For example, appropriate results can be achieved even if the above-described techniques are performed in a different order from that in the above-described method, and/or the above-described elements such as systems, structures, devices, and circuits are coupled or combined in different forms from those in the above-described method or are replaced or substituted with other elements or their equivalents.

Therefore, other implementations, other embodiments, and equivalents to the claims are also within the scope of the following claims.

What is claimed is:

1. A diagnosis assistant system for assisting diagnosis of a plurality of diseases based on a fundus image, comprising:
    a fundus image obtaining unit configured to acquire a target fundus image which is a basis for acquiring diagnosis assistance information on a subject;
    a first processing unit configured to, for the target fundus image, obtain a first result related to a first finding of the subject using a first neural network model, wherein the first neural network model is trained on the basis of a first fundus image set;
    a second processing unit configured to, for the target fundus image, obtain a second result related to a second finding of the subject using a second neural network model, wherein the second neural network model is trained on the basis of a second fundus image set which is at least partially different from the first fundus image set;
    a third processing unit configured to determine, on the basis of the first result and the second result, a diagnostic information on the subject; and
    a diagnostic information output unit configured to provide the determined diagnostic information to a user;
    wherein, the first finding and the second finding is used for diagnosing different diseases, and
    wherein the first finding is related to an eye disease and the first result indicates whether the subject is normal or not regarding the eye disease, and the second finding is related to a systemic disease and the second result indicates whether the subject is normal or not regarding the systemic disease.

2. The diagnosis assistant system of claim 1, wherein:
    the first neural network model is trained to classify an input fundus image into one of normal label and an abnormal label regarding the first finding, and
    the first processing unit obtains the first result by classifying the target fundus image into one of the normal label or the abnormal label.

3. The diagnosis assistant system of claim 1, wherein:
    the third processing unit determines whether the diagnostic information regarding the target fundus image is a normal information or an abnormal information, considering the first result and the second result together.

4. The diagnosis assistant system of claim 3 wherein:
    the third processing unit determines the diagnostic information of the subject by assigning priority on the abnormal label so that a diagnosis accuracy is improved.

5. The diagnosis assistant system of claim 1,
    wherein when the first label is a normal label of the first finding and the second label is a normal label of the second finding, the third processing unit determines the diagnostic information normal, and
    wherein when the first label is not the normal label of the first finding or the second label is not the normal label of the second finding, the third processing unit determines the diagnostic information abnormal.

6. The diagnosis assistant system of claim 1 wherein:
    the first neural network model includes a first sub neural network model and a second sub neural network model and
    the first result is determined by considering a first prediction value predicted by the first sub neural network model and a second prediction value predicted by the second sub neural network model together.

7. The diagnosis assistant system of claim 1 wherein:
    the first processing unit obtains a CAM(class activation map) related to the first label via the first neural network model and
    the diagnostic information output unit output an image of the CAM.

8. A diagnosis assistant system for assisting diagnosis of a plurality of diseases based on a fundus image, comprising:
    a fundus image obtaining unit configured to acquire a target fundus image which is a basis for acquiring diagnosis assistance information on a subject;
    a first processing unit configured to, for the target fundus image, obtain a first result related to a first finding of the subject using a first neural network model wherein the first neural network model is trained on the basis of a first fundus image set;
    a second processing unit configured to, for the target fundus image, obtain a second result related to a second finding of the subject using a second neural network model, wherein the second neural network model is trained on the basis of a second fundus image set which is at least partially different from the first fundus image set;
    a third processing unit configured to determine, on the basis of the first result and the second result, a diagnostic information on the subject; and
    a diagnostic information output unit configured to provide the determined diagnostic information to a user,
    wherein, the first finding and the second finding is used for diagnosing different diseases, and wherein the first finding is related to a first eye disease and the first result indicates whether the subject is normal or not regarding the first eye disease, and the second finding is related to a second eye disease and the second result indicates whether the subject is normal or not regarding the second eye disease.

9. The diagnosis assistant system of claim 8 wherein:
the first processing unit obtains a CAM(class activation map) related to the first label via the first neural network model and
the diagnostic information output unit output an image of the CAM.

10. The diagnosis assistant system of claim 8, wherein:
the third processing unit determines whether the diagnostic information regarding the target fundus image is a normal information or an abnormal information, considering the first result and the second result together.

11. The diagnosis assistant system of claim 10, wherein:
the third processing unit determines the diagnostic information of the subject by assigning priority on the abnormal label so that a diagnosis accuracy is improved.

12. The diagnosis assistant system of claim 10,
wherein when the first label is a normal label of the first finding and the second label is a normal label of the second finding, the third processing unit determines the diagnostic information normal, and
wherein when the first label is not the normal label of the first finding or the second label is not the normal label of the second finding, the third processing unit determines the diagnostic information abnormal.

13. The diagnosis assistant system of claim 8, wherein:
the first neural network model includes a first sub neural network model and a second sub neural network model and
the first result is determined by considering a first prediction value predicted by the first sub neural network model and a second prediction value predicted by the second sub neural network model together.

14. The diagnosis assistant system of claim 8, wherein:
the first processing unit obtains a CAM(class activation map) related to the first label via the first neural network model and the diagnostic information output unit output an image of the CAM.

15. A diagnosis assistant system for assisting diagnosis of a plurality of diseases based on a fundus image, comprising:
a fundus image obtaining unit configured to acquire a target fundus image which is a basis for acquiring diagnosis assistance information on a subject;
a first processing unit configured to, for the target fundus image, obtain a first result related to a first finding of the subject using a first neural network model wherein the first neural network model is trained on the basis of a first fundus image set;
a second processing unit configured to, for the target fundus image, obtain a second result related to a second finding of the subject using a second neural network model, wherein the second neural network model is trained on the basis of a second fundus image set which is at least partially different from the first fundus image set;
a third processing unit configured to determine, on the basis of the first result and the second result, a diagnostic information on the subject;
a diagnostic information output unit configured to provide the determined diagnostic information to a user; and
a fourth processing unit configured to obtain a quality information of the target fundus image,
wherein, the first finding and the second finding is used for diagnosing different diseases, and
wherein, the diagnostic information output unit outputs the quality information of the target fundus image obtained by the fourth processing unit.

16. The diagnosis assistant system of claim 15, wherein:
the first neural network model is trained to classify an input fundus image into one of normal label and an abnormal label regarding the first finding, and
the first processing unit obtains the first result by classifying the target fundus image into one of the normal label or the abnormal label.

17. The diagnosis assistant system of claim 16, wherein:
the third processing unit determines whether the diagnostic information regarding the target fundus image is a normal information or an abnormal information, considering the first result and the second result together.

18. The diagnosis assistant system of claim 17, wherein:
the third processing unit determines the diagnostic information of the subject by assigning priority on the abnormal label so that a diagnosis accuracy is improved.

19. The diagnosis assistant system of claim 15,
wherein when the first label is a normal label of the first finding and the second label is a normal label of the second finding, the third processing unit determines the diagnostic information normal, and
wherein when the first label is not the normal label of the first finding or the second label is not the normal label of the second finding, the third processing unit determines the diagnostic information abnormal.

20. The diagnosis assistant system of claim 15,
wherein when the quality information of the target fundus image is determined to lower than a predetermined quality level in the fourth processing unit,
the diagnostic information output unit provides an information indicating that the quality information of the target fundus image is lower than the predetermined quality level.

* * * * *